United States Patent
Safir et al.

(10) Patent No.: US 12,161,307 B2
(45) Date of Patent: Dec. 10, 2024

(54) DEVICES AND METHODS FOR REDUCING FLUID IN THE IMAGING FIELD OF A TISSUE HANDLING APPARATUS FOR IMPROVING BIOPSY SYSTEM IMAGING QUALITY

(71) Applicant: HOLOGIC, INC., Marlborough, MA (US)

(72) Inventors: Fareeha Safir, Brighton, MA (US); Joseph A. Stand, III, Holden, MA (US); Jacqueline Carano, Shrewsbury, MA (US); Thomas H. Fisk, Newton, MA (US); Tom Farbizio, Patterson, NY (US)

(73) Assignee: Hologic, Inc., Marlborough, MA (US)

( * ) Notice: Subject to any disclaimer, the term of this patent is extended or adjusted under 35 U.S.C. 154(b) by 682 days.

(21) Appl. No.: 16/609,350

(22) PCT Filed: May 3, 2018

(86) PCT No.: PCT/US2018/030975
§ 371 (c)(1),
(2) Date: Oct. 29, 2019

(87) PCT Pub. No.: WO2018/204710
PCT Pub. Date: Nov. 8, 2018

(65) Prior Publication Data
US 2020/0187923 A1    Jun. 18, 2020

Related U.S. Application Data

(60) Provisional application No. 62/500,915, filed on May 3, 2017.

(51) Int. Cl.
*A61B 10/02*    (2006.01)
*A61B 10/00*    (2006.01)
*B01L 3/00*    (2006.01)

(52) U.S. Cl.
CPC ...... *A61B 10/0275* (2013.01); *A61B 10/0096* (2013.01); *A61B 10/0283* (2013.01);
(Continued)

(58) Field of Classification Search
CPC ............ A61B 10/0275; A61B 10/0096; A61B 10/0283; B01L 3/502; B01L 2300/0681; B01L 2400/049
(Continued)

(56) References Cited

U.S. PATENT DOCUMENTS 4,038,988 A    8/1977    Perisse
4,134,012 A    1/1979    Smallbone et al.
(Continued)

FOREIGN PATENT DOCUMENTS

DE    20 2019 106 995    1/2020
EP    2007287    6/2016
(Continued)

OTHER PUBLICATIONS

PCT International Preliminary Report on Patentability in Application PCT/US2018/030975, mailed Nov. 14, 2019, 12 pages.
(Continued)

*Primary Examiner* — Eric J Messersmith
*Assistant Examiner* — Chanel J Jhin
(74) *Attorney, Agent, or Firm* — Merchant & Gould P.C.

(57) ABSTRACT

A tissue holder assembly for receiving and imaging severed tissue samples from a biopsy device includes a base and a cover removably attached to the base to define an interior, the base having one or more vacuum lumens in communication with the interior, the assembly further including a tissue tray removably and rotatably mounted in the interior, wherein a bottom of the tissue tray comprises a filter material that allows fluid to pass through. The cover has a tissue sample entry port formed therein and configured
(Continued)

direct severed tissue samples and fluid aspirated therethrough into a respective tissue storage compartment of the tissue tray positioned under the tissue sample entry port, wherein the base includes a raised surface underlying at least a portion of the tissue tray circumferentially spaced apart from the tissue sample entry port when the cover is attached to the base.

9 Claims, 11 Drawing Sheets

(52) U.S. Cl.
CPC ....... *B01L 3/502* (2013.01); *B01L 2300/0681* (2013.01); *B01L 2400/049* (2013.01)

(58) Field of Classification Search
USPC ......................................................... 600/562
See application file for complete search history.

(56) References Cited

U.S. PATENT DOCUMENTS

| | | |
|---|---|---|
| 4,306,570 A | 12/1981 | Matthews |
| 4,549,554 A | 10/1985 | Markham |
| 4,658,834 A | 4/1987 | Blankenship et al. |
| 4,802,195 A | 1/1989 | Wojciechowski |
| 4,803,639 A | 2/1989 | Steele |
| 4,837,795 A | 6/1989 | Garrigus |
| 4,852,560 A | 8/1989 | Hermann, Jr. |
| 5,023,894 A | 6/1991 | Yamashita |
| 5,023,895 A | 6/1991 | McCroskey |
| 5,256,160 A | 10/1993 | Clement |
| 5,427,742 A | 6/1995 | Holland |
| 5,456,689 A | 10/1995 | Kresch et al. |
| 5,491,344 A | 2/1996 | Kenny et al. |
| 5,505,210 A | 4/1996 | Clement |
| 5,526,822 A | 6/1996 | Burbank et al. |
| 5,541,856 A | 7/1996 | Hammermeister |
| 5,575,293 A | 11/1996 | Miller et al. |
| 5,609,827 A | 3/1997 | Russell |
| 5,754,621 A | 5/1998 | Suzuki |
| 5,983,125 A | 11/1999 | Alfano et al. |
| 6,017,316 A | 1/2000 | Ritchart et al. |
| 6,032,673 A | 3/2000 | Savage et al. |
| 6,058,159 A | 5/2000 | Conway |
| 6,163,590 A | 12/2000 | Wilkins |
| 6,207,111 B1 | 3/2001 | Weinberg |
| 6,225,107 B1 | 5/2001 | Nagle |
| 6,234,672 B1 | 5/2001 | Tomasetti et al. |
| 6,322,522 B1 | 11/2001 | Zimmon |
| 6,403,035 B1 | 6/2002 | Caratsch et al. |
| 6,485,436 B1 | 11/2002 | Truckal et al. |
| 6,535,284 B1 | 3/2003 | Hajduk et al. |
| 6,646,721 B2 | 11/2003 | Compter |
| 6,899,850 B2 | 5/2005 | Haywood |
| 7,166,113 B2 | 1/2007 | Arambula |
| 7,175,612 B2 | 2/2007 | Felix et al. |
| 7,397,894 B2 | 7/2008 | Nakai |
| 7,546,925 B1 * | 6/2009 | Zuk, Jr. .................. B01D 61/18 210/474 |
| 7,616,801 B2 | 11/2009 | Gkanatsios et al. |
| 7,662,109 B2 | 2/2010 | Hibner |
| 7,692,144 B2 | 4/2010 | Watanabe |
| 7,715,523 B2 | 5/2010 | Lafferty |
| 7,753,857 B2 | 7/2010 | Hibner |
| 7,758,601 B2 | 7/2010 | Heywang-Koebrunner et al. |
| 7,854,705 B2 | 12/2010 | Pawluczyk et al. |
| 7,856,081 B2 | 12/2010 | Peschmann |
| 7,858,038 B2 | 12/2010 | Andreyko et al. |
| 7,867,173 B2 | 1/2011 | Hibner et al. |
| 7,869,563 B2 | 1/2011 | DeFreitas et al. |
| 7,881,428 B2 | 2/2011 | Jing et al. |
| 7,972,062 B2 | 7/2011 | Nicolosi |
| 8,038,347 B2 | 10/2011 | Manak |
| 8,038,627 B2 | 10/2011 | Hibner |
| 8,050,735 B2 | 11/2011 | Feke |
| 8,052,616 B2 | 11/2011 | Andrisek et al. |
| 8,162,140 B2 | 4/2012 | Hansen |
| 8,177,728 B2 | 5/2012 | Hibner et al. |
| 8,213,570 B2 | 7/2012 | Panesar |
| 8,217,357 B2 | 7/2012 | Stein et al. |
| 8,235,913 B2 | 8/2012 | Hibner et al. |
| 8,284,896 B2 | 10/2012 | Singh |
| 8,532,745 B2 | 9/2013 | DeFreitas et al. |
| 8,565,374 B2 | 10/2013 | DeFreitas et al. |
| 8,702,623 B2 | 4/2014 | Parihar |
| 8,741,232 B2 | 6/2014 | Baysal |
| 8,764,679 B2 | 7/2014 | Miller et al. |
| 8,787,522 B2 | 7/2014 | Smith et al. |
| 8,873,716 B2 | 10/2014 | Ren et al. |
| 8,911,381 B2 | 12/2014 | Hibner et al. |
| 8,923,603 B2 | 12/2014 | Weston |
| 8,956,306 B2 | 2/2015 | Hibner |
| 8,971,484 B2 | 3/2015 | Beckmann |
| 8,983,030 B2 | 3/2015 | Ookawa |
| 9,020,579 B2 | 4/2015 | Smith et al. |
| 9,066,706 B2 | 6/2015 | DeFreitas et al. |
| 9,068,920 B2 | 6/2015 | Churilla |
| 9,129,715 B2 | 9/2015 | Adler |
| 9,188,696 B2 | 11/2015 | Schafer |
| 9,234,855 B2 | 1/2016 | Watanabe |
| 9,277,895 B2 | 3/2016 | Hara |
| 9,322,790 B2 | 4/2016 | Ookawa |
| 9,326,755 B2 | 5/2016 | Fiebig |
| 9,329,139 B2 | 5/2016 | Itou |
| 9,341,546 B2 | 5/2016 | Stuke |
| 9,347,894 B2 | 5/2016 | Sims |
| 9,492,130 B2 | 11/2016 | Flagle et al. |
| 9,498,175 B2 | 11/2016 | Stein et al. |
| 9,549,709 B2 | 1/2017 | DeFreitas et al. |
| 9,642,581 B2 | 5/2017 | Lowe |
| 9,668,711 B2 | 6/2017 | Smith et al. |
| 9,733,167 B2 | 8/2017 | Wismueller |
| 9,865,424 B2 | 1/2018 | Ikeda |
| 9,901,320 B2 | 2/2018 | DeFreitas et al. |
| 9,943,850 B2 | 4/2018 | Purdy |
| 9,953,799 B2 | 4/2018 | Hakoda |
| 10,008,298 B2 | 6/2018 | King |
| 10,010,296 B2 | 7/2018 | Basu |
| 10,078,093 B2 | 7/2018 | Flagle |
| 10,098,216 B2 | 10/2018 | Kabumoto |
| 10,105,709 B2 | 10/2018 | Purdy |
| 10,145,806 B2 | 12/2018 | Tanaka |
| 10,190,997 B2 | 1/2019 | Aoki |
| 10,194,875 B2 | 2/2019 | DeFreitas et al. |
| 10,201,331 B2 | 2/2019 | Fleming |
| 10,322,412 B2 | 6/2019 | Purdy |
| 10,393,678 B2 | 8/2019 | Watanabe |
| 10,488,351 B2 | 11/2019 | Butani |
| 10,489,964 B2 | 11/2019 | Wang |
| 10,561,387 B2 | 2/2020 | Smith et al. |
| 10,631,809 B2 | 4/2020 | Noh |
| 10,705,030 B2 | 7/2020 | Watanabe |
| 10,709,396 B2 | 7/2020 | Lou |
| 10,729,403 B2 | 8/2020 | DeFreitas et al. |
| 10,753,836 B2 | 8/2020 | O'Driscoll |
| 10,792,003 B2 | 10/2020 | Smith et al. |
| 10,809,208 B2 | 10/2020 | Yashima |
| 10,905,385 B2 | 2/2021 | DeFreitas et al. |
| 11,083,426 B2 | 8/2021 | DeFreitas |
| 11,191,502 B2 | 12/2021 | Smith et al. |
| 11,246,551 B2 | 2/2022 | Butani |
| 11,478,206 B2 | 10/2022 | Smith et al. |
| 11,617,548 B2 | 4/2023 | DeFreitas et al. |
| 2002/0007188 A1 | 1/2002 | Arambula |
| 2002/0145722 A1 | 10/2002 | Compter |
| 2002/0193656 A1 | 12/2002 | Ravins et al. |
| 2003/0087423 A1 | 5/2003 | Haywood |
| 2003/0216730 A1 | 11/2003 | Barry et al. |
| 2004/0022350 A1 | 2/2004 | Gregerson et al. |
| 2004/0174031 A1 | 9/2004 | Rasmussen |
| 2004/0218716 A1 | 11/2004 | Freifeld |
| 2005/0051723 A1 | 3/2005 | Neagle et al. |

(56) References Cited

U.S. PATENT DOCUMENTS

| | | |
|---|---|---|
| 2005/0065453 A1 | 3/2005 | Shabaz et al. |
| 2005/0112034 A1 | 5/2005 | McCormick |
| 2005/0124913 A1 | 6/2005 | Damarati |
| 2005/0148842 A1 | 7/2005 | Wang |
| 2006/0074343 A1 | 4/2006 | Hibner |
| 2006/0116603 A1 | 6/2006 | Shibazaki et al. |
| 2006/0173266 A1 | 8/2006 | Pawluczyk et al. |
| 2007/0106176 A1 | 5/2007 | Mark et al. |
| 2007/0116612 A1 | 5/2007 | Williamson |
| 2007/0166834 A1 | 7/2007 | Williamson, IV et al. |
| 2007/0237684 A1 | 10/2007 | Hansen |
| 2007/0239067 A1 | 10/2007 | Hibner et al. |
| 2007/0270714 A1 | 11/2007 | Cushner et al. |
| 2008/0004545 A1 | 1/2008 | Garrison |
| 2008/0082021 A1 | 4/2008 | Ichikawa |
| 2008/0132805 A1 | 6/2008 | Heywang-Koebrunner et al. |
| 2008/0214955 A1 | 9/2008 | Speeg et al. |
| 2008/0221480 A1 | 9/2008 | Hibner et al. |
| 2008/0228103 A1 | 9/2008 | Ritchie et al. |
| 2008/0249434 A1 | 10/2008 | Hashimshony et al. |
| 2009/0088663 A1 | 4/2009 | Miller et al. |
| 2009/0088666 A1 | 4/2009 | Miller et al. |
| 2009/0131818 A1 | 5/2009 | Speeg et al. |
| 2009/0131820 A1 | 5/2009 | Speeg et al. |
| 2009/0131823 A1 | 5/2009 | Andreyko et al. |
| 2009/0171243 A1 | 7/2009 | Hibner et al. |
| 2009/0171244 A1 | 7/2009 | Ning |
| 2009/0213987 A1 | 8/2009 | Stein |
| 2010/0080346 A1 | 4/2010 | Kalender et al. |
| 2010/0081964 A1 | 4/2010 | Mark |
| 2010/0152611 A1 | 6/2010 | Parihar |
| 2010/0160824 A1 | 6/2010 | Parihar |
| 2010/0160826 A1 | 6/2010 | Parihar |
| 2010/0191145 A1 | 7/2010 | Lafferty |
| 2010/0317997 A1 | 12/2010 | Hibner |
| 2011/0142201 A1 | 6/2011 | Eberhard et al. |
| 2011/0285837 A1 | 11/2011 | Bello |
| 2012/0014504 A1 | 1/2012 | Jang et al. |
| 2012/0051514 A1 | 3/2012 | Sims et al. |
| 2012/0053484 A1 | 3/2012 | Parks |
| 2012/0116246 A1 | 5/2012 | Hibner |
| 2012/0123295 A1 | 5/2012 | Sanbuichi |
| 2012/0245485 A1 | 9/2012 | Hibner |
| 2013/0053724 A1 | 2/2013 | Fiebig |
| 2013/0231585 A1 | 9/2013 | Flagle |
| 2014/0039343 A1 | 2/2014 | Mescher |
| 2014/0051986 A1 | 2/2014 | Zhao et al. |
| 2014/0065656 A1 | 3/2014 | Baysal |
| 2014/0072104 A1 | 3/2014 | Jacobsen et al. |
| 2014/0198893 A1 | 7/2014 | Badawi et al. |
| 2014/0257135 A1 | 9/2014 | DeFreitas |
| 2014/0276209 A1 | 9/2014 | Hibner |
| 2015/0083893 A1 | 3/2015 | Wismueller |
| 2015/0131773 A1 | 5/2015 | Lowe et al. |
| 2015/0209017 A1 | 7/2015 | Fleming |
| 2016/0211045 A1 | 7/2016 | Jeon et al. |
| 2017/0131311 A1 | 5/2017 | Flagle |
| 2017/0309063 A1 | 10/2017 | Wang |
| 2017/0336706 A1 | 11/2017 | Wang |
| 2018/0249985 A1 | 9/2018 | DeFreitas et al. |
| 2019/0054217 A1 | 2/2019 | Axon |
| 2019/0072463 A1 | 3/2019 | O'Driscoll |
| 2019/0167869 A1 | 6/2019 | Willard |
| 2019/0285558 A1 | 9/2019 | DeFreitas |
| 2019/0346471 A1 | 11/2019 | Flagle |
| 2020/0029927 A1 | 1/2020 | Wilson et al. |
| 2020/0061622 A1 | 2/2020 | Purdy |
| 2020/0085393 A1 | 3/2020 | Zhang et al. |
| 2020/0268331 A1 | 8/2020 | Purdy |
| 2020/0352543 A1 | 11/2020 | DeFreitas et al. |
| 2020/0386657 A1 | 12/2020 | O'Driscoll |
| 2022/0015729 A1 | 1/2022 | Purdy et al. |
| 2022/0110597 A1 | 4/2022 | Chen |
| 2022/0133252 A1 | 5/2022 | Smith et al. |
| 2023/0012310 A1 | 1/2023 | Stango |
| 2023/0014922 A1 | 1/2023 | DeFreitas |
| 2023/0121010 A1 | 4/2023 | Smith et al. |
| 2023/0172572 A1 | 6/2023 | Bumdra |
| 2023/0355200 A1 | 11/2023 | Ren |
| 2024/0016461 A1 | 1/2024 | Wolff |

FOREIGN PATENT DOCUMENTS

| | | |
|---|---|---|
| GB | 2018601 | 10/1979 |
| JP | 2014-526937 | 10/2014 |
| JP | 2015-085056 | 5/2015 |
| JP | 2015-520402 | 7/2015 |
| JP | 2016-154878 | 9/2016 |
| JP | 2017099928 | 6/2017 |
| WO | 8101363 | 5/1981 |
| WO | 2007021905 | 2/2007 |
| WO | 2008/025146 | 3/2008 |
| WO | 2009/120206 | 10/2009 |
| WO | 2010/028208 | 3/2010 |
| WO | 2011/140374 | 11/2011 |
| WO | 2012/074885 | 6/2012 |
| WO | 2013/166497 | 11/2013 |
| WO | 2017/060726 | 4/2017 |
| WO | 2018/183086 | 10/2018 |
| WO | WO2018/204710 | 11/2018 |
| WO | 2019/051496 | 3/2019 |
| WO | 2019/085342 | 5/2019 |
| WO | 2019/216766 | 11/2019 |
| WO | 2020/106888 | 5/2020 |
| WO | 2021/202455 | 10/2021 |

OTHER PUBLICATIONS

Watanabe, M. et al., "The quantitative analysis of thin specimens: a review of progress from the Cliff-Lorimer to the new zeta-factor methods", Journal of Microscopy, vol. 221, No. 2, Feb. 1, 2006, p. 91.

English Translation of Notice of Reasons for Rejection in Japanese Patent Application No. 2019-559688, mailed Feb. 22, 2022, 12 pages.

International Search Report and Written Opinion mailed Sep. 25, 2018 for PCT application No. PCT/US2018/030975, applicant Hologic, Inc., 17 pages.

Basak Erguvan-Dogan et al., "Specimen Radiography in Confirmation of MRI-Guided Needle Localization and Surgical Excision of Breast Lesions", American Journal of Roentgenology, American Roentgen Ray Society, vol. 187, No. 2: 339-344 (2006).

* cited by examiner

DEVICES AND METHODS FOR REDUCING FLUID IN THE IMAGING FIELD OF A TISSUE HANDLING APPARATUS FOR IMPROVING BIOPSY SYSTEM IMAGING QUALITY

RELATED APPLICATIONS DATA

The present application is a National Phase entry under 35 U.S.C § 371 of International Patent Application No. PCT/US2018/030975, having an international filing date of May 3, 2018, which claims the benefit under 35 U.S.C. § 119 to U.S. Provisional Patent Application Ser. No. 62/500,915, filed May 3, 2017, which is incorporated by reference in its entirety into the present application.

FIELD

The disclosed inventions generally relate to the preparation of biopsy tissue specimens for imaging, and more particularly, to devices and methods for reducing fluid in an imaging field of a biopsy tissue handling apparatus so that the fluid does not interfere with imaging a tissue sample in the tissue handline apparatus.

BACKGROUND

Biopsies are well-known medical procedures involving the removal of tissue from a living body and examining the tissue for diagnostic study, such as determining the presence, cause or extent of a disease. For example, a biopsy of human breast tissue may be performed for diagnosing breast cancer or other diseases. In generally, a biopsy can be performed by either an open procedure or a percutaneous method. An open surgical biopsy procedure involves making an open incision to the site of the tissue of interest, cutting a sample of the tissue, and removing the tissue through the open incision. A percutaneous biopsy is performed by inserting a biopsy device having a needle and a cutting device through a small incision and advancing the needle and cutting device to the site of the tissue of interest. Then, the cutting device cuts a sample of tissue, and the biopsy device captures the tissue sample and removes the sample through the small incision. Percutaneous biopsy devices have used various means to remove the tissue sample, such as simply removing the device out through the incision with the captured tissue sample, or transporting the tissue sample out through the device (e.g., using a vacuum to aspirate the sample) where it can be removed or drawn through a tube to a container. One advantage of removing the tissue sample from the biopsy device is that multiple samples may be taken without having to remove the biopsy device.

The tissue sample is then examined for diagnosis by imaging the tissue sample using X-ray (while previous X-ray imaging systems recorded on film, more recent X-ray imaging system are digital and record using semiconductor receptors), MRI (magnetic resonance imaging) or other suitable imaging device. For instance, the tissue sample may be placed on an imaging substrate, such as a tissue slide or film, and then placed into the imaging device for taking an image.

Automated biopsy and imaging systems for performing a biopsy and imaging a tissue sample have also been disclosed. For example, U.S. Pat. No. 9,492,130 B2 discloses an integrated biopsy analysis system having a biopsy excision tool, a tissue sample transport mechanism for automatically transporting an excised tissue sample from the biopsy excision tool to an analysis/imaging unit, and an analysis/imaging system for automatically analyzing tissue samples such as imaging using an X-ray imaging device. U.S. Pat. No. 9,492,130 B2 is hereby incorporated by reference herein in its entirety. The disclosed system excises tissue samples, and transfers and places the excised tissue samples into a specimen holder having a plurality of tissue accepting slots for placing a plurality of different tissue samples. The imaging unit is configured to acquire images of the tissue samples in the tissue holder, such as by acquiring individual images of each tissue sample in its respective tissue accepting slot.

SUMMARY

The integrated biopsy systems for performing a biopsy, described above, include a biopsy apparatus for taking a biopsy, as well as an imaging system for acquiring an image of each of the biopsied tissue samples. The excised tissue samples are individually transferred to a sample container of a tissue sample handling apparatus and are then imaged by the imaging system while in the tissue container. Various fluids are present during the process of excising the tissue sample and transporting the tissue sample from the biopsy site on the patient to the tissue sample handling apparatus. For example, bodily fluids such as blood, and surgical solutions such as saline, anesthetic, bio-fluids, etc. may be present at the location of the biopsy (or even flowing through the biopsy apparatus) when taking the tissue sample and/or drawing the tissue sample from the biopsy apparatus. Because the biopsy samples are transported from the biopsy site to the tissue sample handling apparatus through a fluid pathway (e.g., tubing, flow passages, etc.) by a vacuum, these fluids are deposited into the tissue sample handling apparatus along with the tissue samples.

It has been found that fluid in the imaging field (the area being imaged by an imaging device) interferes with the imaging process thereby reducing the quality of the image as compared to an image acquired without the fluid in the imaging field. For example, when acquiring an image using an imaging device, such as an X-ray imaging device, fluid droplets within the imaging field, such as fluid adhered to the bottom of a tissue sample holder, the bottom of a housing holding the tissue sample holder, or even on the surface of a cover above the tissue sample holder, may appear like cancerous tissue or tissue having characteristics indicative of cancer, such as a mass, tumor or calcification, or show up as shadows blocking the image of tissue of interest. The image of the specimen tissue can be used more effectively for diagnosis if the specimen tissue stands out with optimal contrast and sharpness from any surrounding structure of the container or surrounding fluid and that any tissue having characteristics indicative of cancer such as calcifications, masses, cancerous tissue, etc., stand out from the normal tissue. For instance, artifacts in the image may include the container in which a tissue sample is being imaged and other background, such as fluids transmitted with the tissue sample. In addition to effective diagnosis, it is important to confirm that quality images are acquired for immediate assessment of the procedure, including accurate targeting of any lesion, and determining whether any additional samples need to be taken. Taking quality images further increases patient comfort by reducing the time the patient remains under compression during the biopsy procedure and reduces the possibility of needing the patient to return to repeat the procedure because the images were inadequate or incorrect tissue was recovered.

Accordingly, various embodiments of the herein disclosed inventions are directed to devices and methods for reducing fluid from the imaging field of the tissue handling apparatus, including keeping fluid from entering the imaging field and/or removing fluid that enters the imaging field. The tissue handling apparatus (also referred to as a tissue holder assembly) generally comprises a housing having a base, a cover which removably attaches to the base thereby defining an interior space or chamber between the base and the cover, and a tissue holder (also referred to as a tissue tray) which is removably received in the interior space formed by the base and the cover. The base has a bottom member and a cylindrical sidewall extending upward from the bottom member. The base also has one or more vacuum lumens in communication with the chamber of the housing via respective vacuum ports in the sidewall proximate the bottom member. The cover removably attaches onto the base, such as by attaching to the sidewall of the base, thereby defining the interior space or chamber. The cover also has a tissue sample entry port (also referred to as an inlet port) at a sample inlet position located at a first angular position of the housing. The tissue sample entry port is configured to transport biopsied (severed) tissue samples and fluid aspirated therewith from a biopsy excision tool into one of the tissue storage compartments of the tissue holder positioned at the sample inlet position under the tissue sample entry port.

The tissue holder has a plurality of separate tissue storage compartments angularly spaced around the tissue holder. In another aspect, the tissue holder may have a circular shape, and comprise a circular bottom and a circumferential sidewall extending upward from the bottom. The tissue storage compartments may be defined by radial dividing walls extending upward from the bottom, such that each of the tissue storage compartments is wedge-shaped (i.e., pie-shaped, or a sector of a circle, or annular shaped). The tissue holder is rotatable within the housing to position each of the tissue storage compartments at a desired circumferential position, including a sample inlet position for loading a severed tissue sample into a respective tissue storage compartment and an imaging position within an imaging field of an imaging device. When the tissue holder assembly is mounted on the integrated biopsy system, the tissue holder is seated on a drive member to selectively rotate the tissue holder about an axis that is orthogonal or substantially orthogonal with the bottom member of the base.

The housing has an imaging position located at a second angular position of the housing. When installed on an integrated biopsy system, the imaging position of the housing is located in the imaging field of an imaging unit, such as an X-ray imaging device, MRI, or the like. The tissue holder is rotatable within the housing so that the tissue holder can be rotated to position each of the tissue storage compartments at the sample inlet position to receive an excised tissue sample, and at the imaging position to image the excised tissue sample. In one example, the imaging unit is located below the tissue handling apparatus, such that the imaging field extends upwards through the portion of the base located at the imaging position, through the bottom of the tissue holder into the tissue storage compartment located at the imaging position, and up through the portion of the cover located at the imaging position.

Several embodiments of the herein disclosed inventions are directed to devices and methods for removing fluid which accumulates in the tissue storage compartments in which respective tissue samples are deposited and then imaged. For instance, in order to remove fluid from the tissue samples in the tissue storage compartments, it is useful to provide a tissue filter on the bottom of the tissue holder to allow undesired fluid in the tissue sample to be removed prior to imaging. For example, the bottom of the tissue storage compartments may be a filter comprising a porous filter material underlying each of the tissue storage compartments. While most of the fluid in the tissue sample drains through the filter, some fluid adheres to the bottom of the filter due to the numerous small openings in the filter material. Accordingly, one aspect of the disclosed inventions is directed to devices comprising a fluid remover disposed adjacent the bottom of the filter underlying the tissue storage compartment. In one embodiment, the fluid remover comprises a fluid removal reservoir. The fluid removal reservoir is filled with a reservoir fluid, such as saline, which when contacting fluid remnants on the bottom of the filter, removes the fluid remnants. The fluid in the reservoir forms a substantially uniform distribution. When imaging each of the tissue storage compartments within the tissue holder, imaging techniques may be used to remove the image of the substantially uniform fluid from the image of the tissue sample, thereby providing a high-quality image of the tissue sample.

In one example, the fluid is removed by using surface tension that is formed between the reservoir fluid and the fluid remnants. The reservoir has an open top which is in close proximity to the bottom of the tissue holder such that a meniscus of the reservoir fluid contained in the reservoir touches the bottom surface of the filter underlying each tissue storage compartment as each tissue storage compartment is moved across the reservoir. The bottom surface of the filter is moved across the reservoir such that the reservoir fluid (e.g., a meniscus formed by the reservoir fluid) in the reservoir contacts the bottom surface of the filter and removes fluid from the filter underlying the tissue storage compartment. In one way, the tissue storage compartment and filter may be translated relative to the fluid removal reservoir. Alternatively, the fluid removal reservoir may be moved relative to the bottom surface of the filter.

In another embodiment of the disclosed inventions, the fluid removal reservoir may be replaced by a wetted fluid wiper having a wetted blade or other wetted contact surface which the filter moves across to remove fluid remnants.

In still another embodiment, a fluid removal member is fixedly positioned between the bottom member of the base and the bottom of the tissue holder. For instance, the fluid removal member may be affixed to the bottom member below the tissue holder. The fluid removal member has a top surface which contacts, or is in close proximity, to the bottom of the tissue holder (e.g., the tissue filter) such that it dislodges and/or removes fluid cohesively attached to the bottom of the tissue holder as the tissue holder rotates over the fluid removal member.

In another aspect, the fluid removal member may have any suitable shape, such as a cylindrical block, a substantially cylindrical block, an elliptical block, a rectangular block, or other suitable shape. The fluid removal member may have a substantially straight top surface which is a substantially uniform distance from the bottom of the tissue holder, or an arcuate top surface such that a middle portion of the fluid removal member is closer to the bottom of the tissue holder than respective end portions of the fluid removal member.

The operation of the tissue holder assembly will now be described. Tissue samples are deposited into one or more of the tissue storage compartments. The tissue holder is then rotated by the drive member such that the meniscus of the reservoir fluid contained in the reservoir touches the bottom surface of the filter underlying a first tissue storage compartment thereby removing fluid remnants from the bottom surface of the filter and such that the first tissue storage compartment is positioned in an imaging field of an imaging device. An image of the first tissue sample is acquired using the imaging device. The tissue holder is then rotated such that meniscus of the reservoir fluid touches the bottom surface of the filter underlying a second tissue storage compartment thereby removing fluid remnants and such that the second tissue storage compartment is positioned in the imaging field. The imaging device acquires an image of a second tissue sample contained in the second tissue storage compartment. This process is repeated until the meniscus removes fluid remnants, if any, from the filter underlying each of the tissue storage compartments and an image is acquired of each of the respective tissue samples in each of the tissue storage compartments.

In another aspect, the fluid remover may include more than one fluid removal reservoir. For instance, in the tissue holder assembly described above, the fluid remover may have a first fluid removal reservoir as described, and a second fluid removal reservoir angularly spaced apart from the first fluid removal reservoir. For example, the second fluid removal reservoir can be spaced approximately the angular spacing of the tissue storage compartments, or it may be spaced apart 180° so that the first and second fluid removal reservoirs are on opposite sides of the base (and opposite sides of the circular tissue holder).

In another embodiment, the tissue storage compartments of the tissue holder are arranged in a line or array and the tissue holder is moved linearly to move the tissue storage compartments relative to the fluid remover.

In yet another embodiment, the tissue holder assembly utilizes a second embodiment of the base (referred to as a second base) which is different than the first base as described above. The second base is similar to the first base, except that it does not have the fluid removal reservoir on the bottom member, and instead the bottom member has a raised surface (e.g., the raised surface may be attached to the bottom member) within the sidewall of the base. The raised surface underlies at least a portion of the tissue holder circumferentially spaced apart from the tissue sample entry port, such as being located at the imaging position (the second angular position of the housing). The raised surface is designed to reduce fluid getting in the imaging field of the imaging device.

In another aspect of the second base, the raised surface comprises a downward sloping ramp with respect to the bottom of the tissue holder in at least one of a radially outward direction, a clockwise rotational direction and a counterclockwise direction such that fluid getting on the raised surface tends to flow down the slope ramp and off the raised surface. This removes fluid from the imaging field because the raised surface is circumferentially positioned in the imaging field. In still another aspect of the second base the raised surface is integrally formed with the bottom member.

In another aspect of the second base, the raised surface may extend radially outward to a circumferential perimeter wall such that the perimeter wall and sidewall of the base together form an annular fluid flow channel between them.

In another aspect of the second base, the one or more vacuum lumens comprises a first vacuum lumen in communication with a first vacuum port circumferentially located under the tissue sample entry port (at the first angular position of the housing), and a second vacuum lumen in communication with a second vacuum port circumferentially spaced apart from the first vacuum port.

In another aspect of the second base, the bottom member may include a fluid removal vacuum compartment (e.g., the fluid removal vacuum compartment may be attached to the bottom member) underlying the tissue sample entry port when the cover is attached to the second base. The vacuum compartment comprises walls extending upward from the bottom member to form a reservoir having an open top. A vacuum lumen proximate the bottom member is in fluid communication with the vacuum compartment and with a respective vacuum port to aspirate fluid out of the vacuum compartment. When tissue samples and fluid are aspirated through the tissue sample entry port while loading tissue sample into the respective storage compartments of the tissue holder, the vacuum compartment aspirates the fluid out of housing thereby preventing or at least reducing such fluid from getting into the imaging field.

In another aspect, the second base may be configured with the vacuum compartment and without the raised surface.

In still another embodiment, the tissue holder assembly utilizes a second embodiment of the cover (referred to as a second cover) which is different than the first cover as described above. The second cover is similar to the first cover, except that it has a vaulted compartment circumferentially positioned in the imaging field, i.e., positioned at the imaging position, such as above the raised surface when it is attached to the second base. The vaulted compartment comprises a localized area of the cover in which top surface of the cover in the area of the vaulted compartment is higher than the top surface of the surrounding cover. The vaulted compartment shields the top surface of the cover within the imaging field from fluid splashing into the tissue storage compartment underlying the tissue sample entry port. Again, this reduces the amount of fluid getting into the imaging field, thereby improving the quality of the images taken of the tissue samples in the respective storage compartments of the tissue holder.

Accordingly, embodiments described herein provide innovative devices and methods for removing fluid from a surface of tissue filter of a tissue storage compartment so that the fluid does not interfere with imaging tissue in the tissue storage compartment thereby allowing better images of the tissue samples to be taken.

BRIEF DESCRIPTION OF THE DRAWINGS

The foregoing and other aspects of embodiments of the herein disclosed inventions are described in further detail with reference to the accompanying drawings, wherein like reference numerals refer to like elements and the description for like elements shall be applicable for all described embodiments wherever relevant.

DETAILED DESCRIPTION

Figure 1:
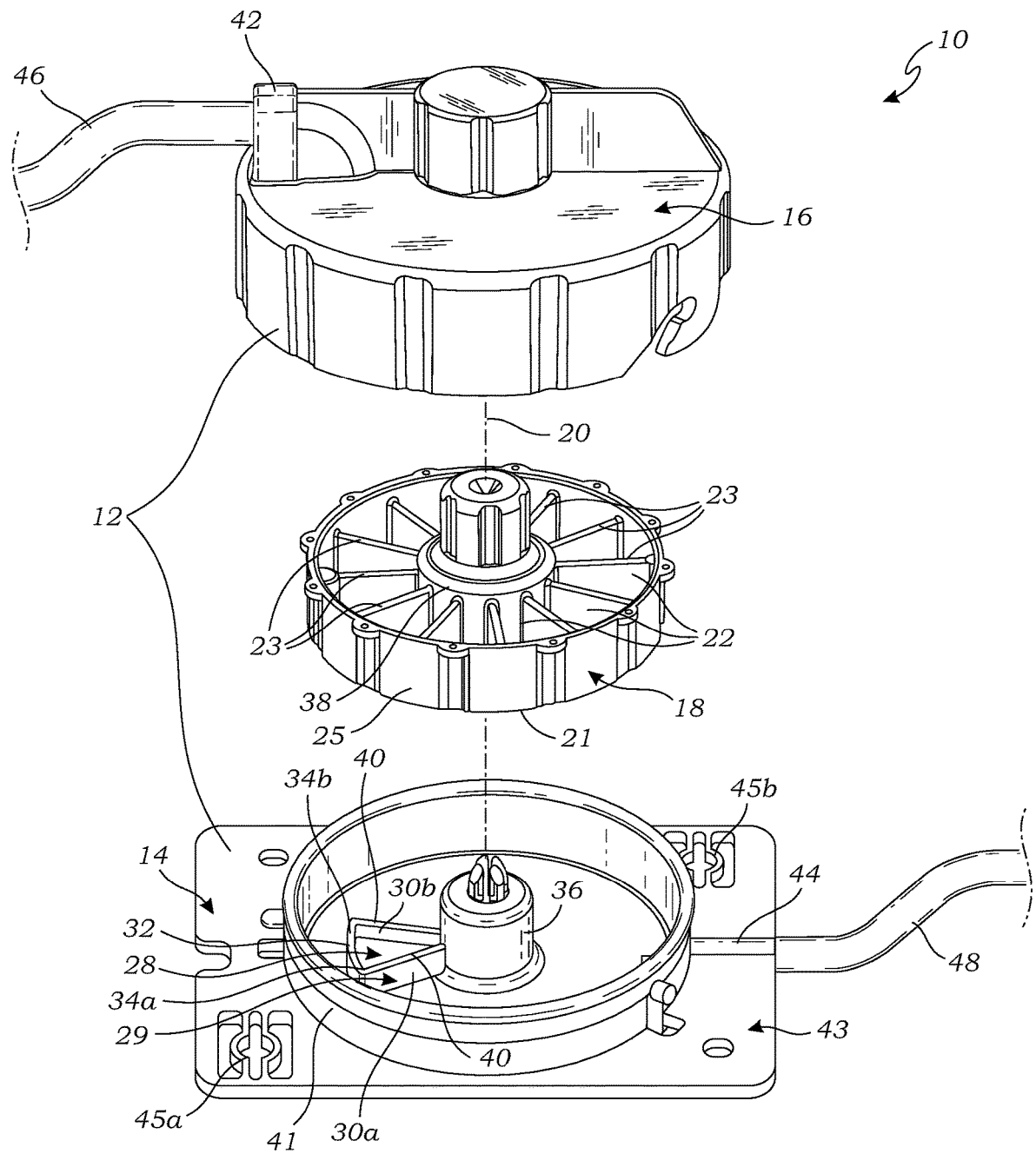
FIG. 1 is a front, perspective exploded view of a tissue hold assembly, according to one embodiment.
Figure 2:
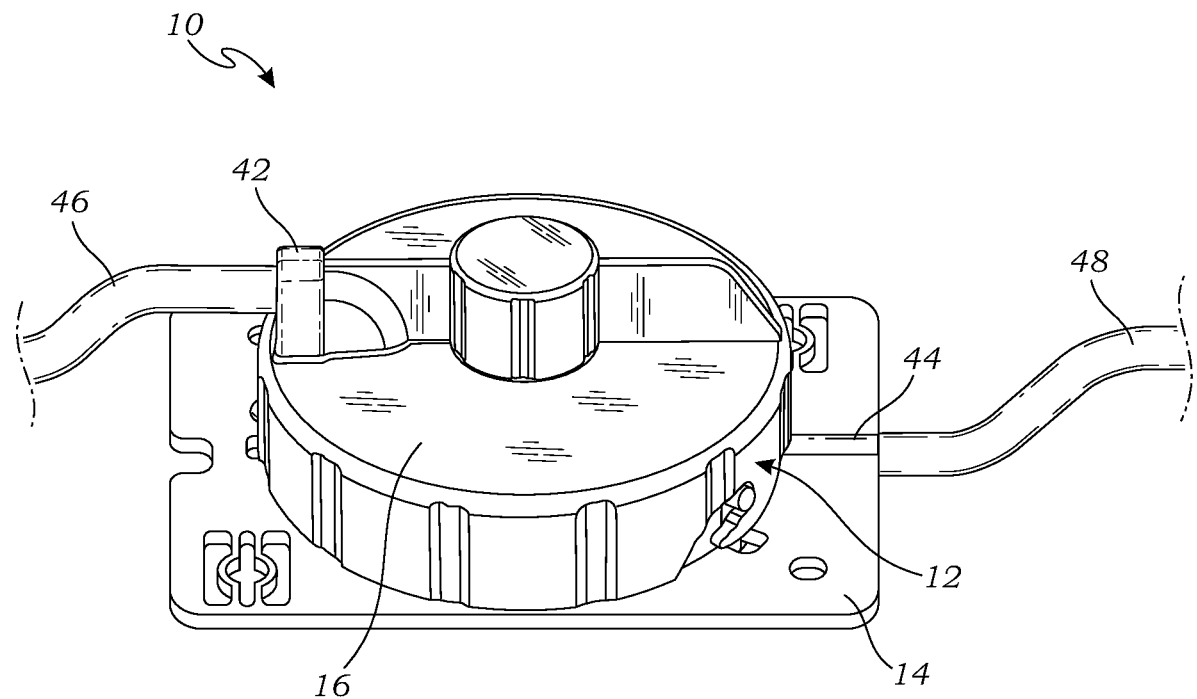
FIG. 2 is a front, perspective view of the tissue holder assembly of FIG. 1 as assembled, according to one embodiment.
Figure 3:
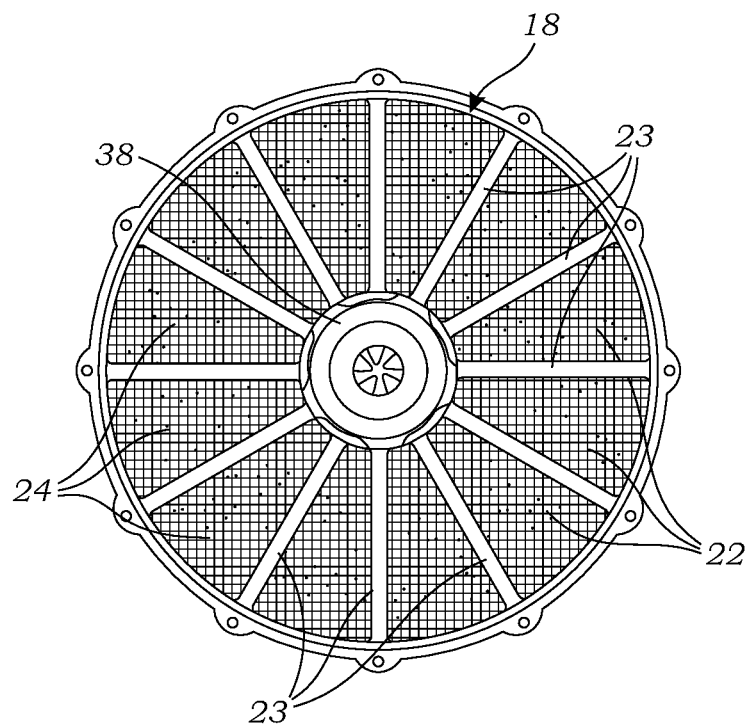
FIG. 3 is a top view of the tissue holder of the tissue holder assembly of FIGS. 1 and 2, according to one embodiment.

FIGS. 1-3 illustrate one embodiment of a tissue holder assembly 10 for receiving a plurality of tissue samples. The tissue holder assembly 10 has a fluid removal reservoir for removing fluid from a filter underlying the bottom of a plurality of tissue storage compartments in order to improve the quality of images acquired of tissue samples in the tissue storage compartments.

The tissue holder assembly 10 includes a housing 12 having a base 14 and a cover 16 which removably attaches onto the base 14. The base 14 and attached cover 16 form an interior or chamber in which a tissue holder 18 is enclosed. The base 14 has a spindle 36 which receives a hub 38 of the tissue holder 18, such that the tissue holder 18 is rotatable relative to the housing 12 about an axis 20. In other words, the base 14 and cover 16 remain stationary and the tissue holder 18 rotates within the chamber formed by the base 14 and cover 16. The tissue holder 18 may be rotated using any suitable actuator, such as a magnetic drive system which rotates the tissue holder 18 using a magnetic field which exerts magnetic force on a magnet or magnetizable element disposed on the tissue holder 18.

The base 14 has a bottom member 43 and a cylindrical sidewall 41 extending upward from the bottom member 43. The bottom member 43 may comprise a substantially flat plate. The bottom member 43 has a plurality of retaining clips 45a, 45b which removably attach to mating retainers on a chassis, frame, housing, or the like, of a tissue biopsy system 50 (see FIG. 4). A spindle 36 is attached to the bottom member 43 and extends upward from the bottom member 43. The tissue holder 18 has a bottom 21 and a circumferential sidewall 25 extending upward from the bottom 21. The tissue holder 18 also has a plurality of tissue storage compartments 22 (in this case, the tissue holder 18 has 13 tissue storage compartments 22, but any number of compartments 22 can be used) arranged angularly around the tissue holder 18. The tissue storage compartments 22 are defined by radial dividing walls 23 extending radially from the hub 38 to the sidewall 25. The tissue storage compartments 22 (also referred to as tissue containers 22) are separated, and partially formed, by radially extending compartment walls 23. In this exemplary embodiment, the tissue holder 18 has a circular shape such that the tissue storage compartments 22 are wedge-shaped (i.e., pie-shaped, sector of a circle), or a sector of an annulus shape in the case that the central part of each tissue storage compartment 22 does not extend all the way to the axis 20. The tissue containers 22 connect to a hub 38 of the tissue holder 18 that is centrally located at the axis 20. The hub 38 is circular and has an opening that allows the spindle 36 of the base 14 to fit through the opening.

The bottom of the tissue holder 18 comprises a tissue filter 24 comprising a porous filter material. The tissue filter 24 may be a single filter, such as a filter sheet, which covers the entire bottom of the tissue holder 18. Alternatively, the tissue filter 22 may be individual filters disposed on the bottom of each tissue storage compartment 22. A fluid removal reservoir 28 is also disposed in the interior formed by the base 14 and the cover 16. The fluid removal reservoir 28 may be attached to the bottom member 43 and is located underneath the tissue holder 18. In this exemplary embodiment, the fluid removal reservoir 28 is formed by a reservoir wall 29 and the bottom member 43 of the base 14. The fluid reservoir 28 may be filled with fluid from the inlet port 46, as further described below. During operation, as fluid from the tissue holder 18 is removed, the fluid in the reservoir 28 may overflow into the base 14.

The reservoir wall 29 includes two side walls 30a and 30b, a first side wall 30a and a second side wall 30b, an outer wall 32 which connects the outer ends 34a and 34b of the first side wall 30a and second side wall 30b, and an inner wall 33 formed by a spindle 36 of the base 14, such that the reservoir wall 29 forms a substantially sector-shaped structure. The spindle 36 of the base 14 rotatably receives a hub 38 of the tissue holder 18 such that the tissue holder 18 may rotate relative to the base 14.

The reservoir wall 29 (at least the side walls 30 and the outer wall 32) has a top edge 40. In the assembled state of the tissue holder assembly 10, the top edge 40 is in close proximity, but not touching, the bottom of the tissue filter 24. The term "close proximity" means that the top edge 40 is close enough to the bottom of the tissue filter 24 such that when the reservoir 28 is filled to the top edge 40 with reservoir fluid, a meniscus formed by the reservoir fluid contacts the bottom surface of the tissue filter 24. Fluid is drawn away from the tissue filter 24 of the tissue container 22, as each of the tissue containers 22 is rotated over the reservoir 28. Said in another way, a fluid path is formed between the fluid within the tissue container 22 and the fluid within the reservoir 28. The fluid path allows the fluid within the tissue container 22 to be drawn out from the tissue container 22 to the reservoir 28. As described above, the fluid in the reservoir 28 forms a substantially uniform distribution. When imaging each of the tissue containers within the tissue holder 18, imaging techniques are used to remove the image of the substantially uniform fluid from the image of the tissue sample, thereby providing a high-quality issue of the tissue sample.

Figure 4:
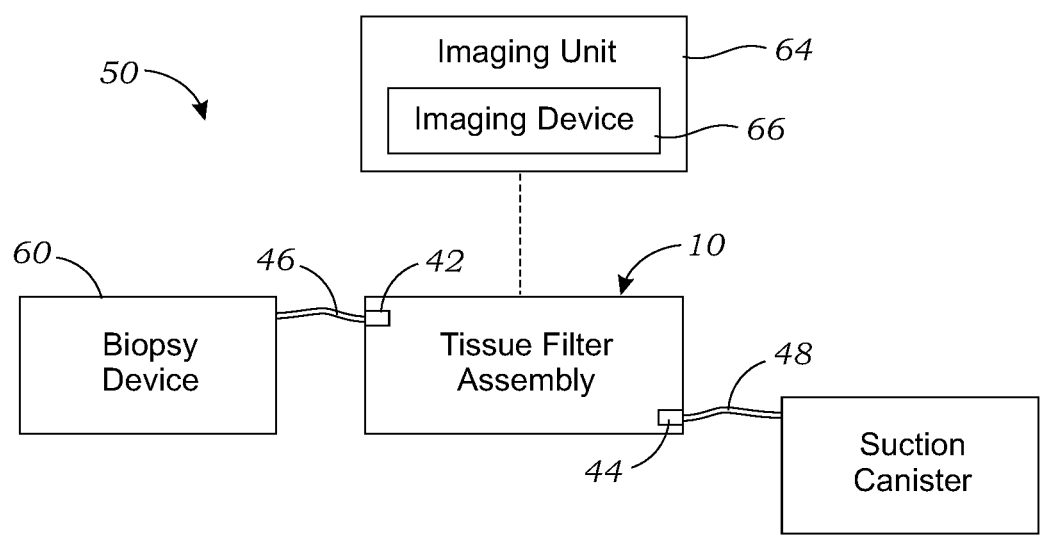
FIG. 4 is a schematic view of a biopsy system comprising the tissue holder assembly of FIG. 1, according to one embodiment.

The tissue holder assembly 10 has a tissue sample entry port 42 (also referred to as inlet port 42) on the cover 16 to which an inlet tube 46 is connected (see FIG. 4). The other end of the inlet tube 46 is connected to a biopsy excision tool 60 (see FIG. 4) such that tissue samples excised by the biopsy excision tool 60 are transported from the biopsy excision tool 60 through the inlet tube 46, into the tissue holder assembly 10 and into one of the tissue storage compartments 22. The tissue holder assembly 10 has an outlet port 44 (also referred to as a vacuum port 44) on the base 16 to which a suction tube 48 is connected. The outlet port 44 extends from outside the interior of the housing 12 into the interior, such as through the sidewall 41. The other end of the suction tube 48 is connected to the suction canister 62 or another suitable vacuum source. The vacuum port 44 draws liquid and/or other material out of the base, and also provides a vacuum within the chamber formed by the housing 12 for drawing tissue samples through the inlet port 42 to be deposited in the respective tissue storage compartments 22 of the tissue holder 18.

Each side wall 30a,b extends radially from an inner end at the connection to the spindle 36 to the outer end 34a,b where they connect to the outer wall 32, which is further from the axis 20. In this described embodiment, the outer end 34a,b of each side wall 30a,b and top edge 40a,b does not extend radially outward as far as the radially outermost part of the tissue storage compartments 22. In other words, the side walls 30 are shorter than the tissue storage compartments 22, such that as the tissue storage compartments 22 are rotated relative to the fluid removal reservoir 28, the fluid removal reservoir 28 moves across less than the entire length of the bottom surface of the tissue filter 24 forming the bottom of a tissue storage compartment 22 and therefore, does not remove fluid from all of the surface of the filter for the tissue storage compartment 22. This leaves room for a magnet on the outer circumference of the bottom of the tissue holder 18 to be able to rotate with tissue holder 18 without hitting the side walls 30a,b and end wall 32 of fluid removal reservoir 28. Alternatively, the side walls 30a,b and top edges 40a,b of the fluid removal reservoir 28 may extend the entire radial length of the tissue storage compartments 22 in order to remove fluid from the entire bottom surface of the filter across the entire bottom of each tissue storage compartment 22. In this case, the outer wall 32 of the fluid removal reservoir may be formed by the sidewall 41 of the base 14.

When the system is activated, the reservoir 28 is filled with fluid to the top edge 40 from the inlet tube 46. During operation, as more fluid is pulled from the tissue containers 22, the fluid from the reservoir 28 may overflow into the base 14. The fluid may then be suctioned out using the suction tube 48.

Referring to FIG. 4, a schematic of a tissue biopsy system 50 is shown. While the schematic of FIG. 4 only shows certain features of the biopsy system 50, the biopsy system 50 may be the biopsy system as disclosed in U.S. Pat. No. 9,492,130 B2, referenced above, and may include any of the features disclosed therein. The biopsy system 50 includes the tissue holder assembly 10, attached to a biopsy excision tool 60 and a suction canister 62. The biopsy system also includes an imaging unit 64 configured to capture images of tissue samples contained in each of the tissue storage compartments 22. The imaging unit 64 has an imaging device 66, such as an X-ray imaging device 66, or other suitable imaging device for capturing images. The imaging device 66 has an imaging field in which the imaging device 66 can acquire an image of material positioned in the imaging field.

Figure 5:
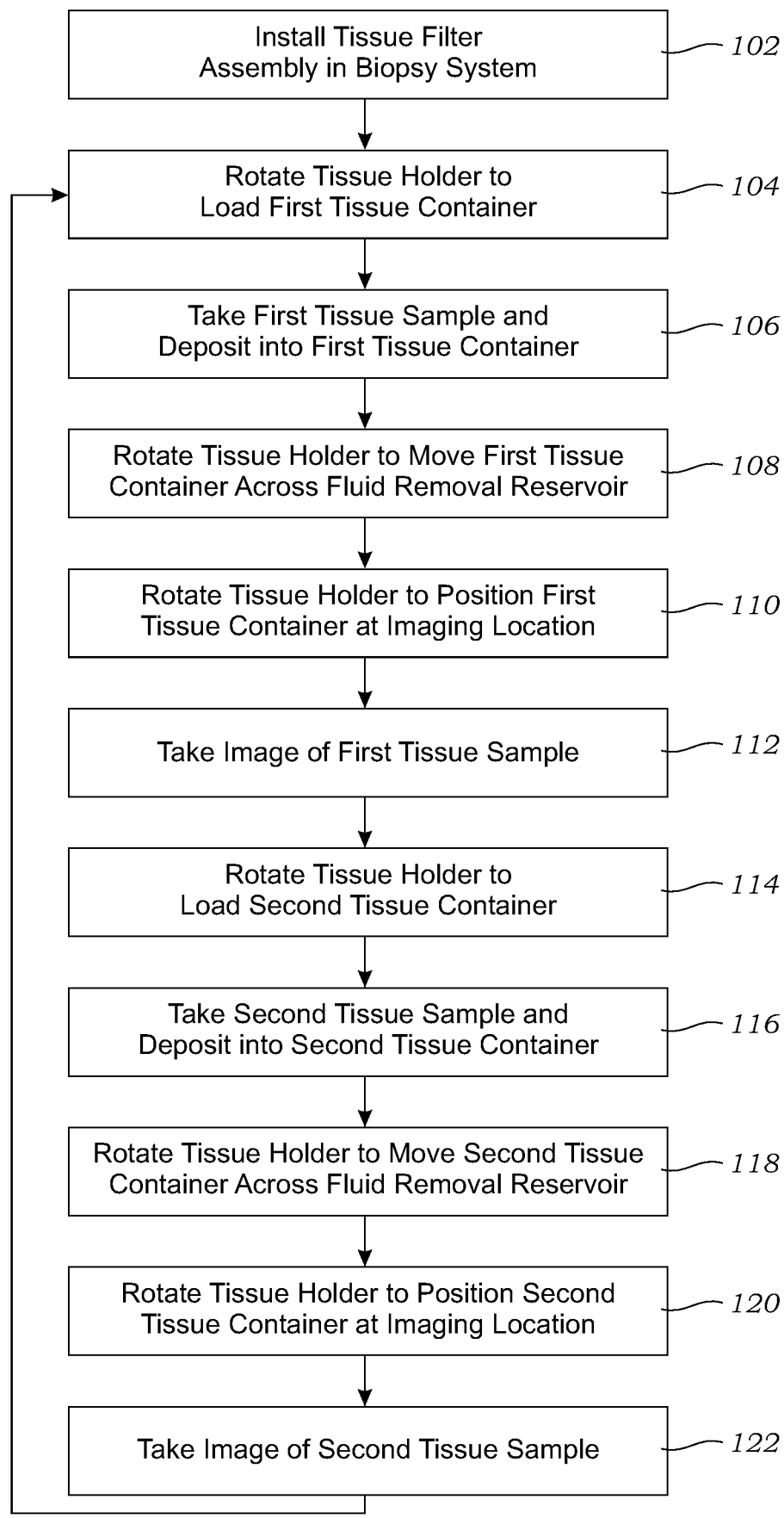
FIG. 5 illustrates a flow chart of a method for using and/or operating the tissue holder assembly of FIG. 1, according to one embodiment.

With reference to FIG. 5, a method 100 of using and operating the tissue holder assembly 10 will now be described. At step 102, the tissue holder assembly 10 is installed into an automated biopsy system 50, such as a system as described in U.S. Pat. No. 9,492,130 B2, described above, with the biopsy excision tool 60 connected to the inlet tube 46, and a vacuum source connected to the suction tube 48. The fluid removal reservoir 28 is filled with reservoir fluid from the inlet tube 46 such that a meniscus of the reservoir fluid extends above the top edge 40 of the wall 29. The tissue holder assembly 10 or just the tissue holder 18 (e.g., a tissue holder 18 may be installed into the tissue holder assembly which is installed in the system 50) may be manually installed in the automated biopsy system 50, or the system 50 may include a robot which is configured to automatically install the tissue holder assembly 10 or just the tissue holder 18 into the system 50.

At step 104, the tissue holder 18 is rotated to position a first tissue storage compartment 22 at a loading position of the tissue filter holder 18 such that a tissue sample transported through the inlet port 42 will be deposited into the first tissue storage compartment 22 of the tissue holder 18. At step 106, a first tissue sample is excised using the biopsy excision tool 62, and the first tissue sample is transported through the inlet tube 46 and inlet port 42 and is deposited into the first tissue storage compartment 22 of the tissue holder 18. At step 108, the tissue holder 18 is rotated such that the bottom surface of the filter 24 underlying the first tissue storage compartment 22 moves across the fluid removal reservoir 28 with the bottom surface of the filter 24 contacting the meniscus of the reservoir fluid and thereby removing fluid remnants accumulated on the bottom surface of the filter 24 underlying the first tissue storage compartment 22. At step 110, the first tissue storage compartment 22 is positioned in the imaging field of the imaging unit 64 to acquire an image of the first tissue sample in the first tissue storage compartment 22. The imaging field may be located just past the fluid removal reservoir 28 in the direction of the movement of the first tissue storage compartment 22 in step 108 such that the first tissue storage compartment 22 is positioned in the imaging field by the movement of the tissue holder 18 in step 108. At step 112, an image of the first tissue sample is acquired using the imaging unit 64.

At step 114, the tissue holder 18 is rotated to position a second tissue storage compartment 22 at the loading position of the tissue holder 18 such that a tissue sample transported through the inlet port 42 can be deposited into the second tissue storage compartment 22. This positioning may occur during the same movement as step 108 and/or 110. In other words, as the first tissue storage compartment 22 is moved across the fluid removal reservoir 28, the second tissue storage compartment 22 may be positioned at the loading position. At step 116, a second tissue sample is excised using the biopsy excision tool 60, and the second tissue sample is transported through the inlet tube 46 and inlet port 42 and is deposited into the second tissue storage compartment 22 of the tissue holder 18. At step 118, the tissue holder 18 is rotated such that the bottom surface of the filter 24 underlying the second tissue storage compartment 22 moves across the fluid removal reservoir 28 with the bottom surface of the filter 24 contacting the meniscus of the reservoir fluid thereby removing fluid remnants accumulated on the bottom surface of the filter 24 of the second tissue storage compartment 22.

At step 120, the second tissue storage compartment 22 is positioned in the imaging field the imaging unit 64 to acquire an image of the second tissue sample in the second tissue storage compartment 22. Again, the imaging field may be located just past the fluid removal reservoir 28 in the direction of the movement of the second container 22 in step 118 such that the second tissue storage compartment 22 is positioned in the imaging field by the movement of the tissue holder 18 in step 118. At step 122, an image of the second tissue sample is acquired using the imaging unit 64. The process is repeated until all of the desired tissue samples have been obtained, deposited into a tissue storage compartment 22 and images have been acquired of all of the respective tissue samples in each of the tissue storage compartments 22.

Alternatively, images of the tissue samples in the tissue storage compartments 22 may be acquired after all the samples are acquired. First, all of the tissue samples are obtained and deposited into respective tissue storage compartments 22 by rotating each tissue storage compartment 22 to the loading position, excising a tissue sample, and depositing the tissue sample into its respective tissue storage compartment 22. Then, the tissue holder 18 is rotated to remove the fluid from each of the tissue containers 22 in the tissue holder 18 and the tissue samples in the tissue holder assembly 10 are imaged. The tissue samples may be imaged all at once by taking a single image of all the tissue containers 22 in the tissue holder 18, processing the image to identify the individual containers 22 and separating each image from each container 22. Alternatively, the tissue holder 18 may be rotated to acquire a separate image of each of the containers until images have been taken of all of the respective tissue samples in each of the tissue containers 22. In yet another embodiment, the tissue holder assembly 10 is placed in an imaging unit, such as an X-ray imaging device. In a manual system, the filter assembly 10 may be manually installed in the imaging unit 54.

In an automated and integrated system such as the system described above, the tissue holder assembly 10 is already located in the imaging unit 64 while performing the biopsy excisions, or a robot may place the tissue holder assembly 10 in the imaging unit 64. The tissue holder 18 is then rotated to move a tissue storage compartment 22 across the fluid removal reservoir 28, the tissue storage compartment 22 is positioned in the imaging position, and an image is acquired using the imaging unit 64. This process is repeated for each of the tissue storage compartments 22 having a tissue sample to be imaged.

In an alternative embodiment, instead of fluid reservoir 28, the tissue holder assembly 10 may use a gas nozzle located in a similar position as the fluid removal reservoir 28 and directed at the bottom surface of the filter 24. The gas nozzle may have a fan-like spreader nozzle to create a wide air flow which directs gas (e.g., air) flow across the entire length, or a substantial portion of the length, of the tissue storage compartments 22. Hence, the gas nozzle is connected to a source of pressurized gas (such as compressed air), and as the tissue storage compartments 22 are moved across the path of the gas from the gas nozzle, the gas removes fluid stuck to the bottom surface of the filter, similar to the fluid removal reservoir 28, described above. The use and operation of the gas nozzle embodiment is basically the same as that described for the tissue holder assembly 10, described above.

Figure 6:
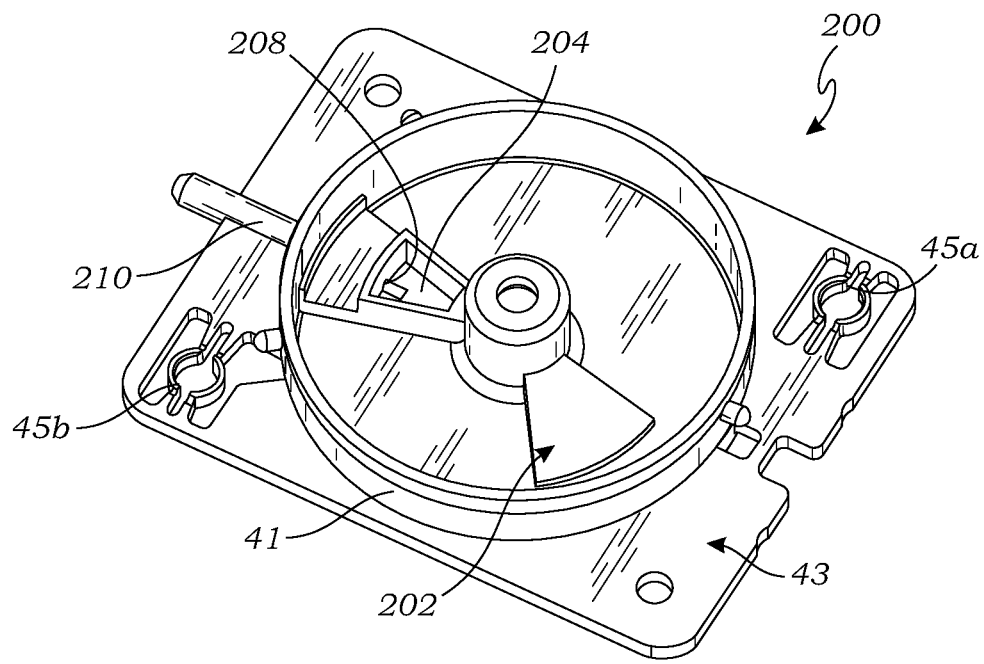
FIG. 6 is a top perspective view of another embodiment of a base for use with a tissue holder assembly, according to another embodiment.
Figure 13:
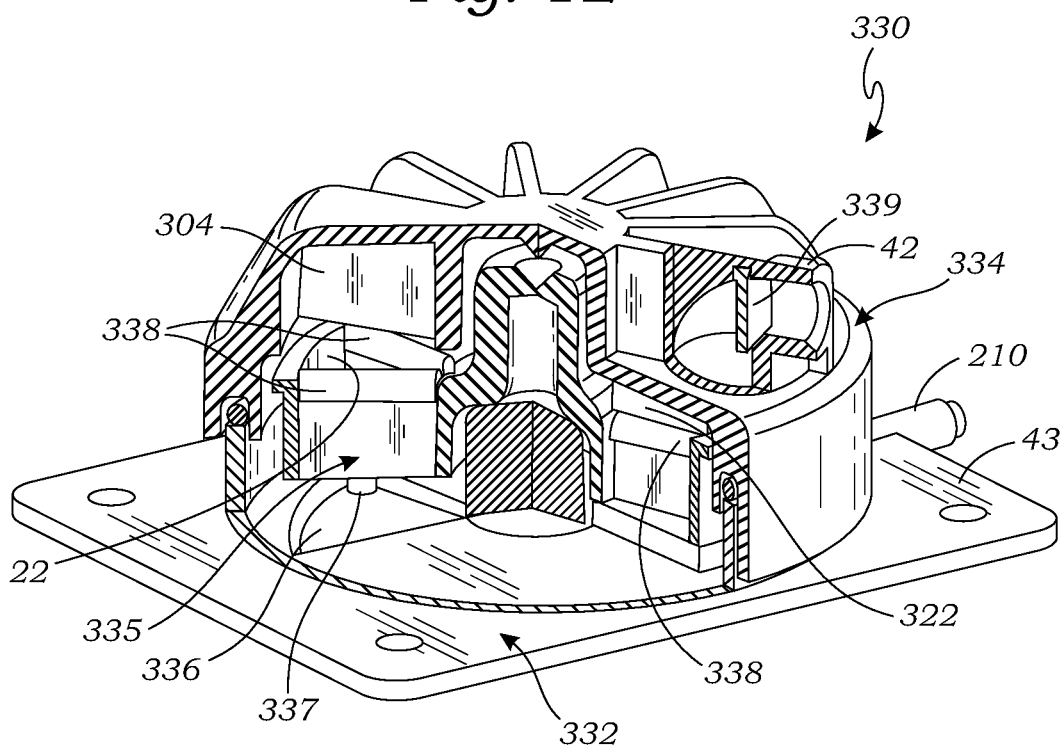
FIG. 13 is a side, perspective, cut-away view of another embodiment of a tissue holder assembly, according to another embodiment.

FIG. 6 illustrates another embodiment of a base 200 which is configured to be used as the base in any of the tissue holder assemblies described herein, including the tissue holder assembly 10, the tissue holder assembly 300 (see FIG. 10), and the tissue holder assembly 330 (see FIG. 13). The base 200 is similar to the base 14, described above, except that it does not have the fluid removal reservoir 28 of base 14, and instead it has a raised surface 202 underlying the imaging field of the imaging device 66 and a vacuum compartment 204 on the bottom member 43 underlying the tissue sample entry port 42. The raised surface 202 and vacuum compartment 204 cooperate to reduce fluid in the imaging field of the imaging device 66. In particular, the vacuum compartment 204 directly underlying the tissue sample entry port 42 draws fluid through the bottom surface 21 of the tissue tray 18, and the raised surface 202 prevents fluid that has already passed through the bottom surface 21 from collecting under the tissue tray 18 in the imaging field of an imaging device 66. In various embodiments, the raised surface 202 may be parallel to the bottom surface 21 of the tissue tray 18, or it may be a downward-sloped ramp in one or more of a radially outward direction, a clockwise rotational direction and a counterclockwise rotational direction such that fluid passing through the tissue filter 24 flows "down" the sloped ramp 202 and away from the imaging field of an imaging device 66.

The raised surface 202 is attached to the bottom member 43 and extends upward from the bottom member 43. The raised surface 202 abuts the hub 36 and extends radially outward from the hub 36 toward the sidewall 41. As shown in the embodiment of FIG. 6, the raised surface 202 does not extend radially outward all the way to the sidewall 41 but stops short of the sidewall 41 to allow room for a magnet or other structure attached to the bottom of the tissue holder 18 to be able to rotate with the tissue holder 18 without hitting the raised surface 202. Alternatively, the raised surface 202 may extend radially outward all the way to the sidewall 41 (e.g., if it will not interfere with the tissue holder 18). The raised surface 202 extends circumferentially through an arc such that it has a sector shape overlying a portion of the bottom member 43 within the sidewall 41 and underlies a portion of the tissue holder 18. The raised surface 202 is circumferentially spaced apart from the inlet port 42 (and/or the vacuum compartment 204) when the cover 16 is installed on the base 200 by at least 150°, or at least 90°, or at least 75°, or at least 45°, or from 45° to 150° (measured from center to center of the respective features).

The top surface 206 of the raised surface 202 is below the bottom of the tissue holder 18 when a tissue holder 18 is installed in the base 200 such that the raised surface 202 does not interfere with the rotation of the tissue holder 18. The top surface 206 slopes downward in a radially outward direction (i.e., the top surface 206 is highest at the inner radius and lowest at the outer radius). Alternatively, or in addition, to being sloped in a radially direction, the top surface 206 may be sloped downward in a rotational direction, either clockwise or counterclockwise. In other words, the top surface 206 may slope downward as it extends circumferentially through an arc.

The raised surface 202 is circumferentially positioned to be in the imaging field of the imaging device 66 when the base is installed on the imaging unit 64. The raised surface 202 minimizes the fluid in the imaging field of the imaging device 66 first by being raised above the bottom member 43 where fluid accumulates, and also by having a slope such that fluid that finds its way onto the top surface 206 of the raised surface 202 runs off due to the slope.

The vacuum compartment 204 is also attached to the bottom member 43 and is circumferentially spaced apart from the raised surface 202. The vacuum compartment 204 has walls extending upward from the bottom member 43 and is open on top. The vacuum compartment does not extend radially outward all the way to the sidewall 41 but stops short of the sidewall 41 to allow room for a magnet or other structure attached to the bottom of the tissue holder 18 to be able to rotate with the tissue holder 18 without hitting the vacuum compartment 204. Alternatively, the vacuum compartment 204 may extend radially outward all the way to the sidewall 41 (e.g., if it will not interfere with the tissue holder 18). The vacuum compartment 204 may have a sector shape extending circumferentially over a portion of the bottom member 43. The vacuum compartment 204 may have a lowered portion 205 at the radially outward portion of the vacuum compartment 204 to provide clearance for the rotating tissue holder 18.

The base 200 has a first vacuum lumen 208 proximate the bottom member 43. The first vacuum lumen 208 is in fluid communication with the vacuum compartment 204 and a first vacuum port 210. The first vacuum port 210 extends from outside the chamber of the housing 12 to the interior where it is in communication with the vacuum lumen 208. The first vacuum port 210 is connected to a vacuum source, such as the suction canister 62 (see FIG. 4), or other suitable vacuum source. The first vacuum port 210 draws liquid and/or other material out of the base 200, and also provides a vacuum within the chamber formed by the housing 12 for drawing (aspirating) tissue samples through the tissue sample entry port 42 to be deposited in the respective tissue storage compartments 22 of the tissue holder 18.

The vacuum compartment 204 is circumferentially positioned under the tissue sample entry port 42 when the cover 16 is assembled onto the base 200. In operation, the vacuum compartment 204 removes fluid entering the chamber of the housing 12 through the tissue sample entry port 42 and reduces fluid splashing onto other parts of the chamber of housing 12. Thus, by providing the vacuum compartment 204, and positioning the sample entry port 42 circumferentially spaced apart from the raised surface 202 (which is at the location of the imaging field), the base 200 reduces the amount of fluid in the imaging field thereby improving the quality of images obtained using the base 200 in a tissue holder assembly 10. It should be appreciated that the raised surface 206 and/or vacuum compartment 208 may be formed integrally with the bottom member 43 or may be formed separately and attached to the bottom member 43. For instance, the raised surface 206 and/or vacuum compartment 208 and bottom member 43 may be injection molded as a single, integral part.

Figure 7:
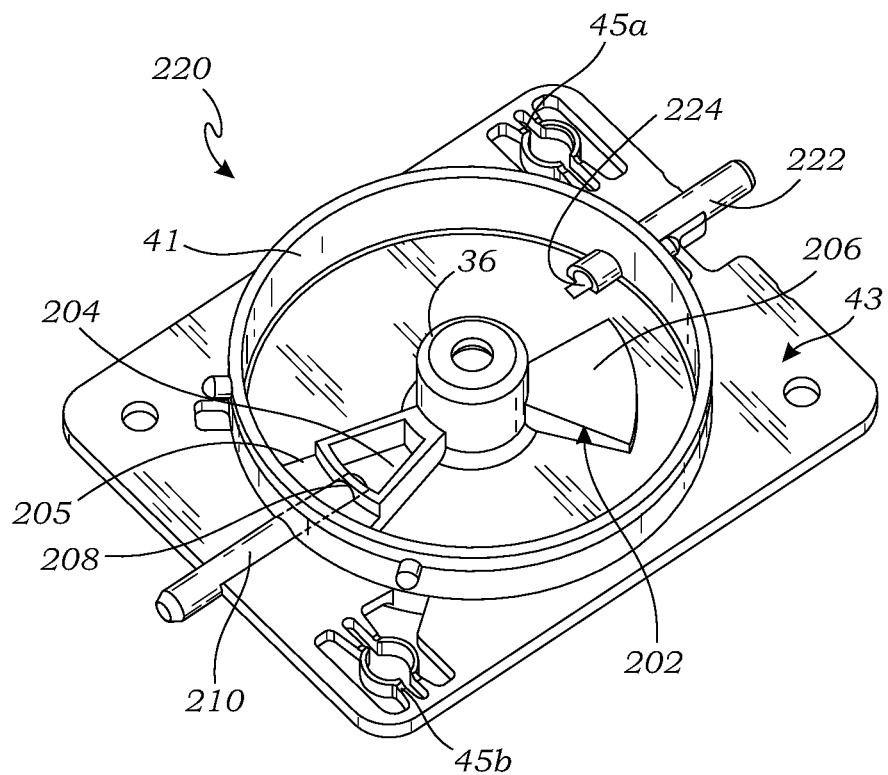
FIG. 7 is a top perspective view of still another embodiment of a base for use with a tissue holder assembly, according to another embodiment.

Turning to FIG. 7, another base 220 is illustrated. The base 220 is also configured to be used as the base in any of the tissue holder assemblies described herein including the tissue holder assembly 10, the tissue holder assembly 300 (see FIG. 10), and the tissue holder assembly 330 (see FIG. 13). The base 220 is the same as the base 200, except that it includes a second vacuum port 222 for removing fluid that may accumulate in the bottom of the chamber of the housing 12. For example, fluid may accumulate in the chamber of the housing 12 outside of the vacuum compartment 204. The second vacuum port 222 is in fluid communication with a second vacuum lumen 224 which is in fluid communication with the chamber of the housing 12. Second vacuum port 222 and second vacuum port 224 are circumferentially spaced apart from the first vacuum port 210 and first vacuum lumen 210, such as by about 180°, or between 150° and 180° (measured from center to center of the respective features).

The second vacuum port 222 extends from outside the chamber of the housing 12 to the interior where it is in communication with the second vacuum lumen 224. The second vacuum lumen 224 is proximate the bottom member 43. The second vacuum port 222 is connected to a vacuum source, such as the suction canister 62 (see FIG. 4) or another suitable vacuum source. The second vacuum port 222 draws liquid and/or other material out of the base 220, and also provides a vacuum within the chamber formed by the housing 12 for drawing (e.g., aspirating) tissue samples through the tissue sample entry port 42 to be deposited in the respective tissue storage compartments 22 of the tissue holder 18.

Figure 8:
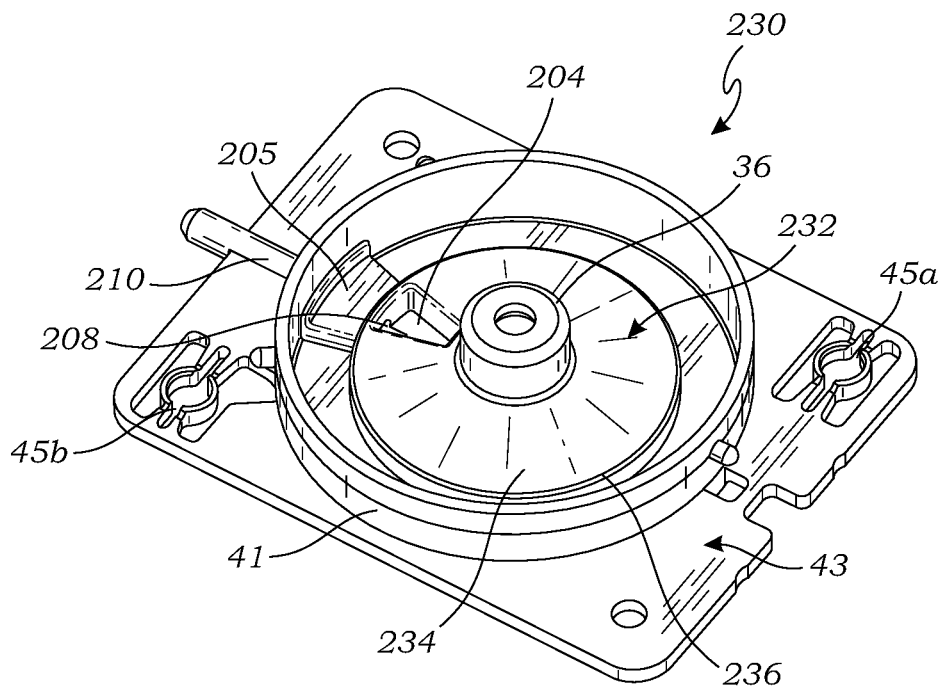
FIG. 8 is a top perspective view of yet another embodiment of a base for use with a tissue holder assembly, according to another embodiment.
Figure 10:
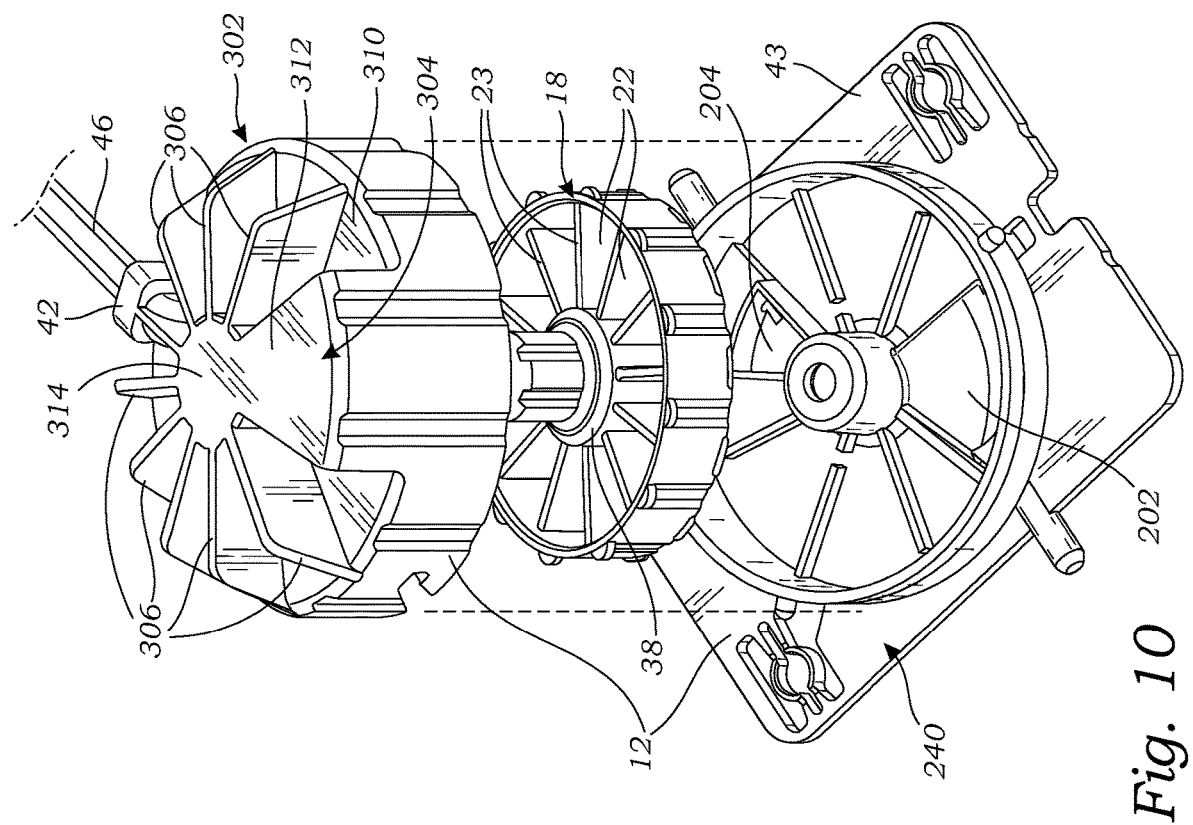
FIG. 10 is a front, perspective exploded view of another embodiment of a tissue holder assembly, according to another embodiment.

FIG. 8 illustrates yet another base 230 configured to be used as the base in any of the tissue holder assemblies described herein, including the tissue holder assembly 10, and the tissue holder assembly 300 (see FIG. 10). The base 230 is the same as the base 200, except that the raised surface 232 extends circumferentially around the entire chamber of the housing 12 except for the circumferential portion occupied by the vacuum compartment 204. In other words, the raised surface 232 extends circumferentially around the chamber except for a portion directly underlying the tissue sample entry port 42 of the cover 16 when the cover 16 is installed on the base 230. Like the raised surface 202, the raised surface 232 has a top surface 234 which slopes downward in a radially outward direction (i.e., the top surface 234 is highest at the inner radius and lowest at the outer radius). The raised surface 232 extends radially outward to a perimeter wall 236. The perimeter wall 236 and sidewall 43 together form an annular fluid flow channel 238 between them.

Similar to the construction of the base 200 and the base 220, the raised surface 232 and/or vacuum compartment 208 may be formed integrally with the bottom member 43, or formed separately and attached to the bottom member 43. For instance, the raised surface 232 and/or vacuum compartment 208 and bottom member 43 may be injection molded as a single, integral part.

Figure 9:
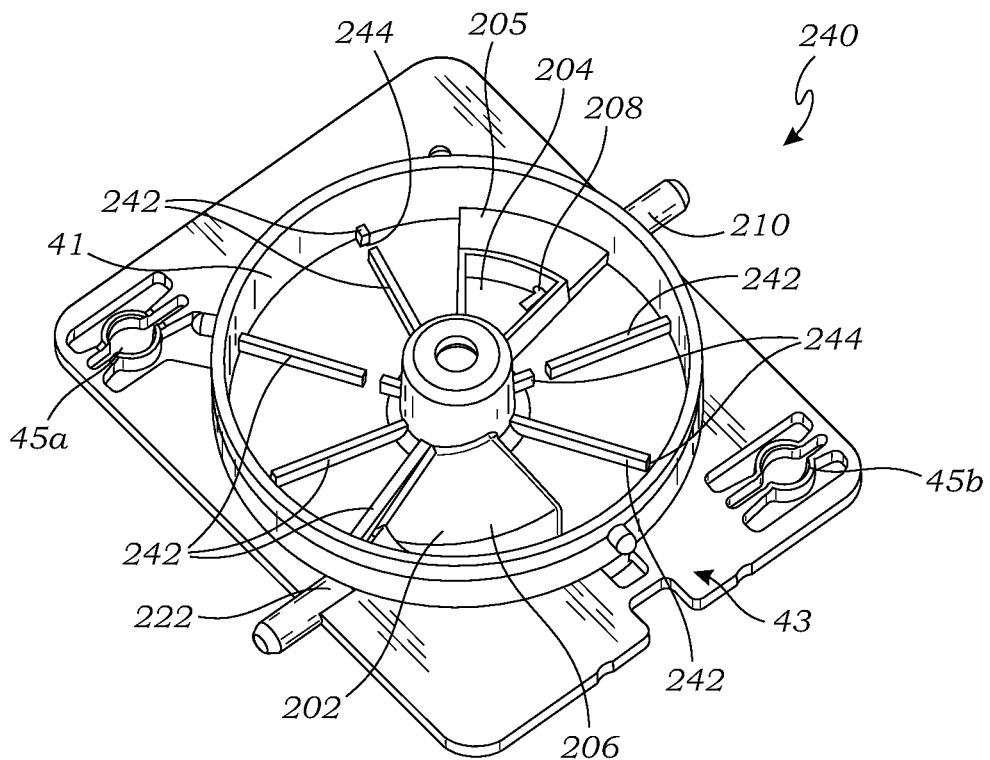
FIG. 9 is a top perspective view of still another embodiment of a base for use with a tissue holder assembly, according to another embodiment.
Figure 11:
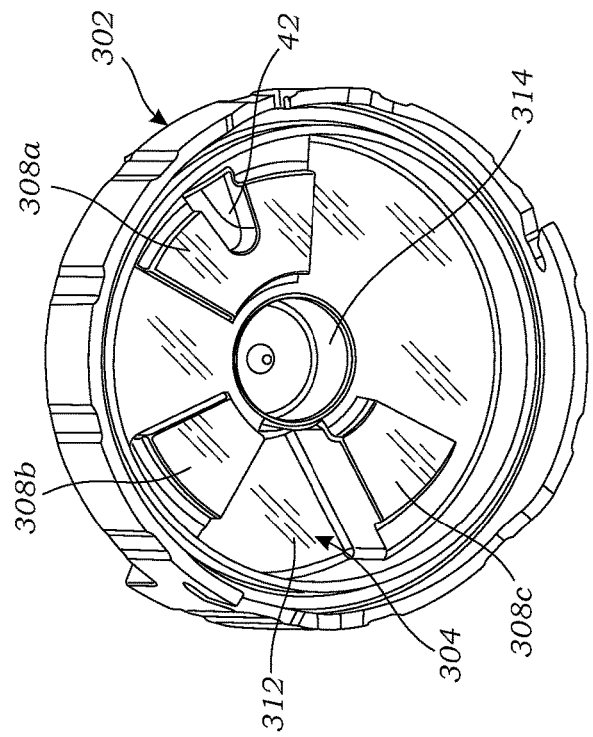
FIG. 11 is a bottom perspective view of the cover of the tissue holder assembly of FIG. 10, according to another embodiment.

FIG. 9 illustrates still another base 240 which is configured to be used as the base in any of the tissue holder assemblies described herein, including the tissue holder assembly 10, the tissue holder assembly 300 (see FIG. 10), and the tissue holder assembly 330 (see FIG. 13). The base 240 is the same as the base 220, except that the base 240 further includes a plurality of reinforcing ribs 242 attached to the bottom member 43 within the sidewall 41. The reinforcing ribs 242 extend radially from the hub 36 to the sidewall 41. The reinforcing ribs 242 provide stiffening of the bottom member 43 to reduce the amount of deformation of the bottom member 43 when a vacuum is pulled within the chamber of the housing 12. The reduced pressure within the chamber of the housing 12 produced by the vacuum causes the higher pressure (atmospheric pressure) on the outside of the chamber to push the bottom member 43 inward which causes the bottom member 43 to deflect inward.

The reinforcing ribs 242 may have gaps 244 to allow fluid to flow past each of the ribs 242 so that fluid can flow circumferentially around the base 240 to the first and second vacuum lumens 208 and 224.

FIG. 10 illustrates another tissue holder assembly 300, which is similar to the tissue holder assembly 10, except that the tissue holder assembly 300 includes the base 240, and an alternative embodiment of a cover 302. The tissue holder 18 in the tissue holder assembly 300 is the same as the tissue holder 18 in the tissue holder assembly 10. The cover 302 is similar to the cover 16, except that the cover 300 has a vaulted compartment 304, a plurality of cover reinforcing ribs 306 and a plurality of baffles 308.

The cover 302, like the cover 16, removably attaches to the base 240 thereby forming a chamber or interior of the housing 12. The cover 302 has a top surface 310 which extends circumferentially around the cover 302, except in the area of the vaulted compartment 304. The inner side of the cover 302 has a vaulted compartment 304 which has a vaulted compartment top surface 312 which is higher than the top surface 310. The vaulted compartment 304 is circumferentially positioned above the raised surface 202 when the cover 302 is secured to the base 240. The vaulted compartment 304 is shielded from fluid flowing in through the tissue sample entry port 42, such as fluid splashing into the respective tissue storage compartments 22 underlying the tissue sample port 42.

The cover 302 also has a plurality of cover reinforcing ribs 306 attached to the outside of the top surface 310 and extending radially from the cover hub 314 to the outer radial edge of the top surface 310. Similar to the reinforcing ribs 242, the cover reinforcing ribs 306 stiffen the cover 302 to reduce deformation of the cover 302 due to the vacuum within the chamber of the housing 12.

The cover 302 further includes a plurality of wide baffles 308a, 308b and 308c. The baffles 308 are lower surfaces of the top surface 310 which form barriers that prevent fluid from passing by the baffles. For example, baffle 308a surrounds the opening of the tissue sample entry port 42 and prevents fluid entering the chamber of the housing through the entry port 42 from flowing or splashing past the baffle 308a. This prevents or reduces fluid from flowing or splashing into the imaging field circumferentially located at the position of the vaulted compartment 304 and the raised surface 302. The baffles 308b and 308c on either side of the vaulted compartment 304 similarly prevents or reduces fluid from entering the chamber of the housing 12 through the entry port 42 from flowing or splashing past the baffles 308b and 308c into the imaging field.

Figure 12:
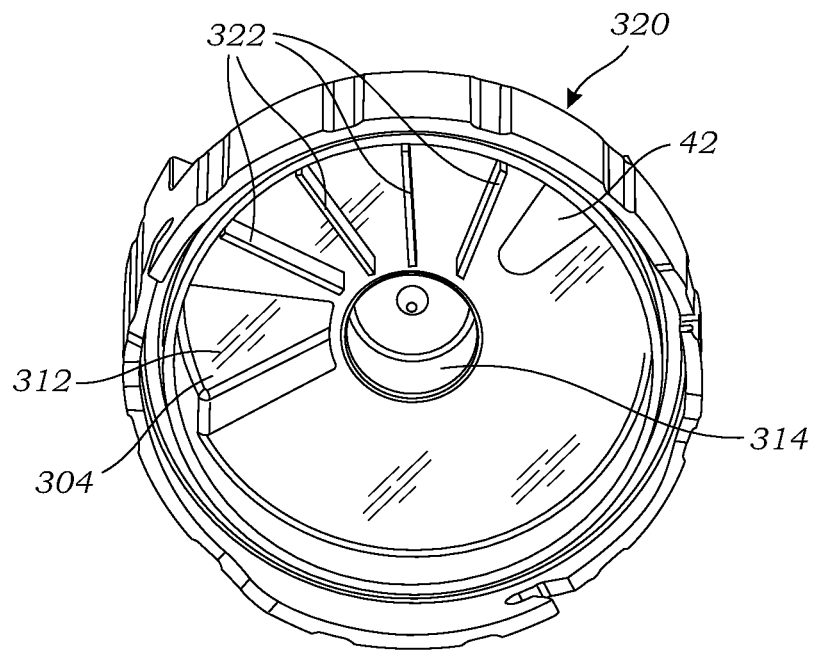
FIG. 12 is a bottom perspective view of another cover for use with a tissue holder assembly, according to another embodiment.

FIG. 12 illustrates another embodiment of a cover 320 which is configured to be used as the cover in any of the tissue holder assemblies described herein, including the tissue holder assembly 10, the tissue holder assembly 300 (see FIG. 10), and the tissue holder assembly 330 (see FIG. 13). The cover 320 is the same as the cover 302, except that the cover 320 does not have the wide baffles 308, but instead has a plurality of narrow baffles 322 extending downward from the inside of the top surface 310. The baffles 322 extend radially from the cover hub 314 to the outer radial edge of the inside of the top surface 310.

FIG. 13 is a cut-away view illustrating another tissue handling assembly 330. The tissue handling assembly 330 is similar to the tissue holder assembly 300, except that the tissue holder assembly 330 includes an alternative embodiment of a base 332, an alternative embodiment of a cover 334, and an alternative embodiment of a tissue holder 335.

The base 332 shown in FIG. 13 is similar to the base 200 described herein, except that instead of the vacuum compartment 208, the base 332 has a fluid drain recess 336. The fluid drain recess 336 is circumferentially positioned at the imaging field of an imaging unit 66. The fluid drain recess 336 is a localized, lowered area of the bottom member 43. The fluid drain recess 336 has a drain lumen 337 which may be connected to a vacuum source to draw for collecting and draining fluid from the imaging field.

The tissue holder 335 in the tissue holder assembly 330 is the same as the tissue holder 18 in the tissue holder assembly 300, except that the tissue holder 335 has a plurality of compliant baffles 338 attached to the top of each of the compartment walls 23. The compliant baffles 338, similar to the baffles 322 and the wide baffles 308, prevent fluid from flowing or splashing from the tissue sample entry port 42 into the imaging field.

The cover 334 is the same as the cover 320, except that the baffles 322 in the cover are compliant baffles, and the cover 320 has a trap door 339. The baffles 322 in the cover 320 may be compliant or rigid because they are not designed to contact anything. The baffles 322 in the cover 334 contact the baffles 338 as the tissue holder 334 rotates, and the respective baffles 322 and baffles 338 bend to allow that baffles to move past each other. The trap door 339 is pivotally attached to the cover 334 within the sample inlet entry 42 so that it pivots back and forth. The trap door 339 slows down samples and/or fluid being aspirated into the sample inlet entry 42 which reduces the splashing of fluid when it is deposited into a respective tissue storage compartment 22 of the tissue holder 335.

Any of the base 332, cover 334, and/or tissue holder 335 may be used with any of the other bases, covers and/or tissue holders described herein to form a tissue holder assembly.

Figure 14:
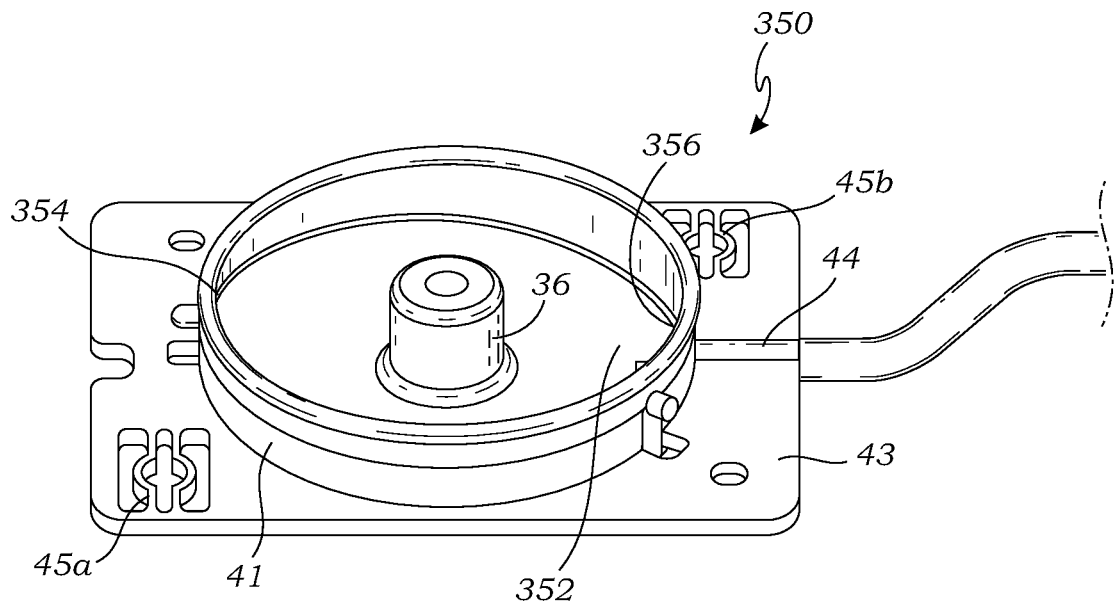
FIG. 14 is a top perspective view of still another embodiment of a base for use with a tissue holder assembly, according to another embodiment.

FIG. 14 illustrates another embodiment of a base 350 which is configured to be used as the base in any of the tissue holder assemblies described herein, including the tissue holder assembly 10, and the tissue holder assembly 300. The base 350 is the same as the base 14, except that the base 350 does not have the fluid removal reservoir 28, and instead has a sloped bottom member 352 within the sidewall 41. The bottom member 352 slopes downward from a high point 354 circumferentially positioned at a location underlying the tissue sample entry port 42 to a low point 354 circumferentially offset from the tissue sample entry port 42, such as offset 180°, or offset between 90° and 180°, or offset between 150° and 180°. The outlet port 44 is located at the low point 354 in order to draw fluid draining down the sloped bottom member 352 out of the housing 12.

Figure 15:
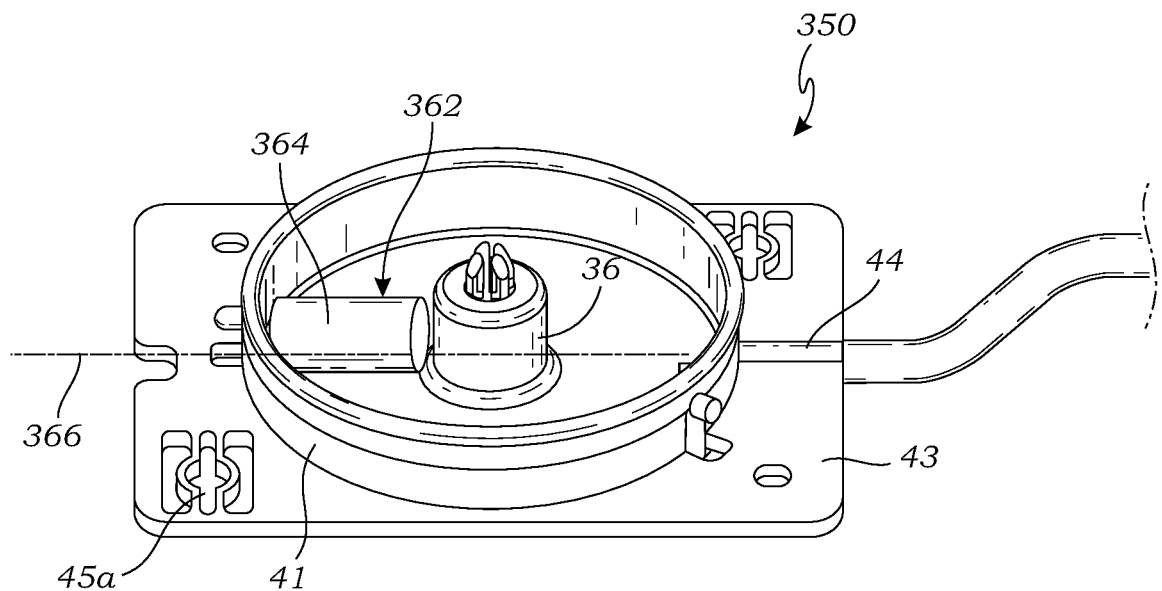
FIG. 15 is a top perspective view of still another embodiment of a base for use with a tissue holder assembly, according to another embodiment.

FIG. 15 illustrates another embodiment of a base 360 which is configured to be used as the base in any of the tissue holder assemblies described herein, including the tissue holder assembly 10, the tissue holder assembly 300 (see FIG. 10), and the tissue holder assembly 330 (see FIG. 13). The base 360 is the same as the base 14, except that the base 360 does not have the fluid removal reservoir 28, and instead has a fluid removal member 362 disposed on the bottom member 43 within the sidewall 41. The fluid removal member 362 has a top surface 364 positioned above the bottom member 43, such that it just contacts the bottom of the tissue storage compartments 22, e.g., the tissue filter 24 forming the bottom of the tissue compartments 22 of the tissue holder 18. The fluid removal member 362 is circumferentially positioned spaced apart from the imaging field of the imaging device 66. For example, the fluid removal member 362 may be circumferentially positioned the equivalent of one, or two, or three storage compartment arc lengths from the imaging field in the clockwise direction or counterclockwise direction. Preferably, the fluid removal member 362 is positioned so that it removes fluid from the tissue filter 24 of a tissue storage compartment 22 just before it rotates into the imaging field to be imaged by the imaging device 66.

In use with a tissue holder 18 installed on the base 360, the top surface 364 contacts the tissue filter 24 and physically dislodges or removes fluid cohesively held in the tissue filter 24 as the tissue holder 18 rotates the tissue filter 24 rotates over the top surface 364 of the fluid removal member 362. Alternatively, the top surface 364 may be located such that the top surface 364 is in close proximity to tissue filter 24 or bottom of the tissue holder 18 such that it is close enough to contact fluid adhering to the bottom of tissue filter 24 or bottom of the tissue holder 18.

In the embodiment of FIG. 15, the fluid removal member 362 comprises a block 362 of compliant material having a cylindrical shape (circular cross-section), or substantially cylindrical shape (elliptical cross-section) or oblong (elliptical cross-section). The block 362 has a longitudinal axis 366 extending radially from the hub 36 toward the sidewall 41. The compliant material may be a polymeric material. The compliant material may be porous such that it can be wetted (e.g., like a sponge) or substantially non-porous. The compliant material may comprise hydrophobic material or hydrophilic material.

Figure 16:
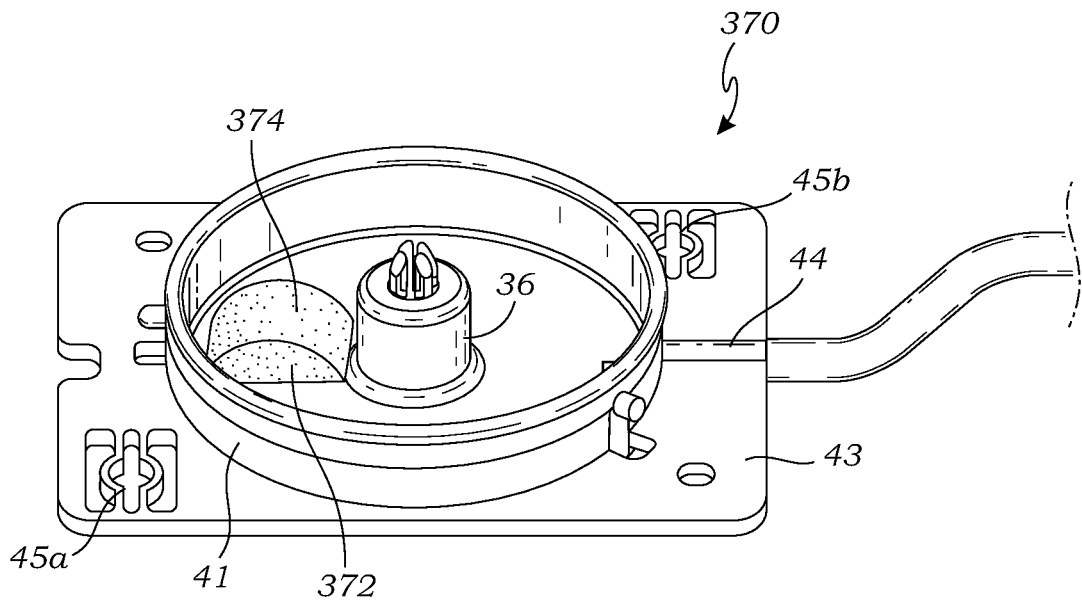
FIG. 16 is a top perspective view of still another embodiment of a base for use with a tissue holder assembly, according to yet another embodiment.

FIG. 16 illustrates another embodiment of a base 370 which is configured to be used as the base in any of the tissue holder assemblies described herein, including the tissue holder assembly 10, the tissue holder assembly 300 (see FIG. 10), and the tissue holder assembly 330 (see FIG. 13). The base 370 is the same as the base 360, except that the fluid removal member 372 of the base 370 has a different shape than the fluid removal member 362 of the base 360. The fluid removal member 372 comprises a block 372 of material having an arched shape such that the top surface 374 is arcuate in a vertical, radial plane extending from the hub 36 to the sidewall 41. The fluid removal member 372 may have all of the applicable features and characteristics described for the fluid removal member 362.

Figure 17:
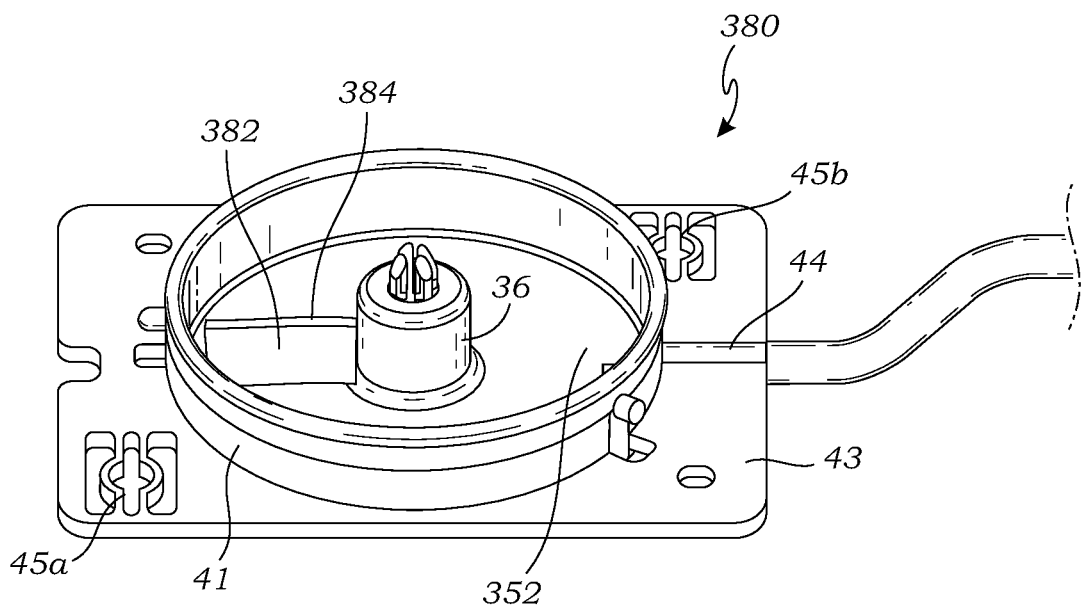
FIG. 17 is a top perspective view of still another embodiment of a base for use with a tissue holder assembly, according to another embodiment.

FIG. 17 illustrates another embodiment of a base 380 which is configured to be used as the base in any of the tissue holder assemblies described herein, including the tissue holder assembly 10, the tissue holder assembly 300 (see FIG. 10), and the tissue holder assembly 330 (see FIG. 13). The base 380 is the same as the base 360, except that the fluid removal member 382 of the base 380 has a different shape than the fluid removal member 362 of the base 360. The fluid removal member 382 comprises a block 382 of material having a rectangular shape such that the top surface 384 is flat and extends radially horizontally from the hub 36 to the sidewall 41. The fluid removal member 382 may have all of the applicable features and characteristics described for the fluid removal member 362.

Figure 18:
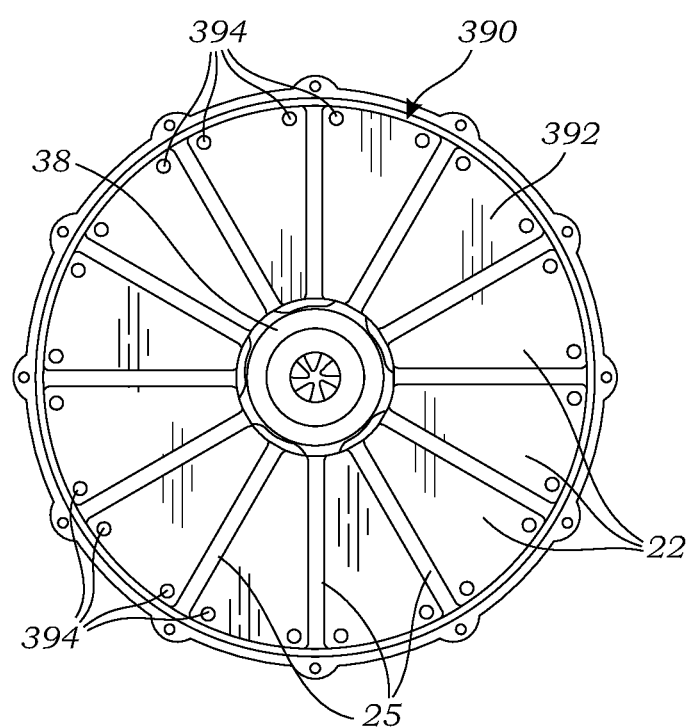
FIG. 18 is a top view of another embodiment of a tissue holder for use with a tissue holder assembly, according to still another embodiment.

FIG. 18 illustrates another embodiment of a tissue holder 390 configured to be used as the tissue holder in any of the tissue holder assemblies described herein, including the tissue holder assembly 10, the tissue holder assembly 300, and the tissue holder assembly 330. The tissue holder 390 is the same as the tissue holder 18, except that instead of having a tissue filter 24 forming the bottom of the tissue storage compartments 24, the tissue holder 390 (and the tissue storage compartments 22) have a solid bottom 392. Each of the storage compartments 24 has one or more fluid egress apertures 394 located proximate where the solid bottom meets the sidewall 25. For example, the fluid egress apertures 394 may be apertures in the bottom 392 located in the radially outer corners of each storage compartment 22, as shown in FIG. 18. One or more additional fluid egress apertures 394 may be included at the radially inward corners of each storage compartment 22, and/or other suitable location.

Although particular embodiments of the disclosed inventions have been shown and described, it is to be understood that the above description is provided for purposes of explanation and illustration only. Thus, various changes and modifications may be made without departing from the scope of the disclosed inventions. For example, not all of the components depicted and described in the disclosed embodiments are necessary, and various additional embodiments of the disclosed inventions may include any suitable combinations of the described components, and the general shapes and relative sizes of the components may be modified. While the systems and methods have been described cytological samples, they can be configured and utilized with any types of samples. Accordingly, embodiments are intended to exemplify alternatives, modifications, and equivalents that may fall within the scope of the claims.

The invention claimed is:

1. A tissue holder assembly configured for receiving and imaging severed tissue samples from a biopsy device, the tissue holder assembly comprising:
   a base;
   a cover which removably attaches onto the base, wherein the base and attached cover define an interior, the base having one or more vacuum lumens in communication with the interior via respective vacuum ports in the base; and
   a tissue tray disposed in the interior, the tissue tray having a plurality of tissue storage compartments, wherein a bottom of the tissue tray comprises a filter material that allows fluid in the respective tissue storage compartments to pass through the filter material,
   wherein the cover has a tissue sample entry port formed therein and configured to direct severed tissue samples and fluid aspirated therethrough into a respective tissue storage compartment of the tissue tray positioned under the tissue sample entry port when the cover is attached to the base, and
   wherein the base comprises a raised surface underlying at least a portion of the tissue tray circumferentially spaced apart from the tissue sample entry port when the cover is attached to the base, wherein the raised surface extends circumferentially through an arc that defines a sector shape, and wherein the raised surface extends radially outward to a circumferential perimeter wall extending upward from a bottom interior surface of the base to the raised surface, the circumferential perimeter wall and an outer sidewall of the base together defining an annular fluid flow channel.

2. The tissue holder assembly of claim 1, wherein a downward sloped ramp is defined by an upper surface of the raised surface.

3. A tissue holder assembly configured for receiving and imaging severed tissue samples from a biopsy device, the tissue holder assembly comprising:
   a base;
   a hub centrally disposed on the base;
   a cover which removably attaches onto the base, wherein the base and attached cover define an interior, the base having one or more vacuum lumens in communication with the interior via respective vacuum ports in the base;
   a tissue tray disposed in the interior, the tissue tray having a plurality of tissue storage compartments, wherein a bottom of the tissue tray comprises a filter material that allows fluid in the respective tissue storage compartments to pass through the filter material,
   wherein the cover has a tissue sample entry port formed therein and configured to direct severed tissue samples and fluid aspirated therethrough into a respective tissue storage compartment of the tissue tray positioned under the tissue sample entry port when the cover is attached to the base; and a raised surface disposed at a level higher than the base and extending both radially outward from the hub and circumferentially through an arc so as to define a sector shape that underlies one of the plurality of tissue storage compartments, wherein the sector shape is circumferentially spaced apart from the tissue sample entry port when the cover is attached to the base, wherein the raised surface extends circumferentially around the interior except for a portion of the interior directly underlying the tissue sample entry port, and wherein the raised surface extends radially outward to a circumferential perimeter wall extending upward from a bottom interior surface of the base to the raised surface, the circumferential perimeter wall and an outer sidewall of the base together defining an annular fluid flow channel.

4. The tissue holder assembly of claim 3, wherein the raised surface comprises a downward sloped ramp with respect to the bottom of the tissue tray in one of a radially outward direction, a clockwise rotational direction or a counterclockwise rotational direction such that fluid passing through the filter material flows down the sloped ramp.

5. The tissue holder assembly of claim 3, wherein the raised surface is integrally formed with the base.

6. The tissue holder assembly of claim 3, wherein the tissue holder assembly is configured to be mounted on or in an imager such that the raised surface is at least partially located within an imaging field of the imager.

7. The tissue holder assembly of claim 3, wherein an inner side of the cover comprises an open vaulted compartment positioned above at least a portion of the raised surface when the cover is secured to the base, such that the vaulted compartment is shielded from liquid splashing into the respective tissue storage compartment underlying the tissue sample entry port.

8. The tissue holder assembly of claim 3, wherein the one or more vacuum lumens comprise a first vacuum lumen in communication with a first vacuum port located under the tissue sample entry port, and a second vacuum lumen in communication with a second vacuum port circumferentially spaced apart from the first vacuum port.

9. The tissue holder assembly of claim 8, wherein the second vacuum port is spaced 180° apart from the first vacuum port.

* * * * *